(12) United States Patent
Milosevic et al.

(10) Patent No.: US 10,882,891 B2
(45) Date of Patent: Jan. 5, 2021

(54) DENDRITIC CELL COMPOSITION

(71) Applicants: MEDIGENE IMMUNOTHERAPIES GMBH, Planegg-Martinsried (DE); HELMHOLTZ ZENTRUM MÜNCHEN DEUTSCHES FORSCHUNGSZENTRUM FÜR GESUNDHEIT UND UMWELT (GMBH), Neuherberg (DE)

(72) Inventors: Slavoljub Milosevic, Munich (DE); Christian Ellinger, Munich (DE); Carina Wehner, Munich (DE); Dolores Schendel, Munich (DE)

(73) Assignees: MEDIGENE IMMUNOTHERAPIES GMBH, Planegg-Martinsried (DE); HELMHOLTZ ZENTRUM MÜNCHEN DEUTSCHES FORSCHUNGSZENTRUM FÜR GESUNDHEIT UND UMWELT (GMBH), Neuherberg (DE)

( * ) Notice: Subject to any disclaimer, the term of this patent is extended or adjusted under 35 U.S.C. 154(b) by 80 days.

(21) Appl. No.: 16/065,037

(22) PCT Filed: Dec. 22, 2016

(86) PCT No.: PCT/EP2016/082445
§ 371 (c)(1),
(2) Date: Jun. 21, 2018

(87) PCT Pub. No.: WO2017/109110
PCT Pub. Date: Jun. 29, 2017

(65) Prior Publication Data
US 2019/0000949 A1  Jan. 3, 2019

(30) Foreign Application Priority Data

Dec. 23, 2015 (EP) .................................. 15202329
Sep. 23, 2016 (EP) .................................. 16190399

(51) Int. Cl.
*C07K 14/47* (2006.01)
*C12N 5/0784* (2010.01)
*A61K 38/00* (2006.01)
*C12N 5/0783* (2010.01)
*A61K 39/00* (2006.01)
*A61P 35/00* (2006.01)
*A61K 35/17* (2015.01)

(52) U.S. Cl.
CPC .......... *C07K 14/4748* (2013.01); *A61K 35/17* (2013.01); *A61K 38/00* (2013.01); *A61K 39/001191* (2018.08); *A61P 35/00* (2018.01); *C12N 5/0638* (2013.01); *C12N 5/0639* (2013.01); *A61K 39/001184* (2018.08); *A61K 2039/5154* (2013.01); *C07K 2319/02* (2013.01); *C07K 2319/03* (2013.01); *C07K 2319/06* (2013.01); *C12N 2501/22* (2013.01); *C12N 2501/2304* (2013.01); *C12N 2501/24* (2013.01); *C12N 2502/1114* (2013.01); *C12N 2506/115* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,703,004 A | 10/1987 | Hopp et al. | |
| 4,851,341 A | 7/1989 | Hopp et al. | |
| 5,591,828 A | 1/1997 | Bosslet et al. | |
| 5,766,886 A | 6/1998 | Studnicka et al. | |
| 6,372,716 B1 | 4/2002 | Bush et al. | |
| 6,566,329 B1 | 5/2003 | Meyn et al. | |
| 6,685,940 B2 | 2/2004 | Andya et al. | |
| 2002/0045241 A1 | 4/2002 | Schendel | |
| 2005/0037421 A1 | 2/2005 | Honda et al. | |
| 2005/0042718 A1 | 2/2005 | Bazin et al. | |
| 2005/0112141 A1 | 5/2005 | Terman | |
| 2005/0136049 A1 | 6/2005 | Ledbetter et al. | |
| 2010/0284976 A1* | 11/2010 | Schendel | A61K 35/15 424/93.7 |
| 2018/0245242 A1 | 8/2018 | Schendel | |
| 2018/0256716 A1 | 8/2018 | Schendel | |

FOREIGN PATENT DOCUMENTS

| | | | |
|---|---|---|---|
| DE | 19625191 A1 | 1/1998 | |
| EP | 0404097 A2 | 12/1990 | |
| EP | 0451216 A1 | 10/1991 | |
| EP | 1910521 A1 | 4/2008 | |

(Continued)

OTHER PUBLICATIONS

Bonehill et al., 2008, MOl. Ther. vol. 16: 1170-1180.*
GenBank Accession DQ668405.1, 2008, pp. 1-2.*
Allard et al., 2008, Vaccine, vol. 26: 3735-3741.*
Wehner, translation of p. 110 and Fig. 4.24 legend, 7 pages. 2020.*
Wehner, google translation of 4.21 Figure legend, 2 pages. 2020.*
Boullart, A.C.I. et al., "Maturation of monocyte-derived dendritic cells with Toll-like receptor 3 and 7/8 ligands combined with prostaglandin E2 results in high interleukin-12 production and cell migration," *Cancer Immunol Immunother* 57:1589-1597, Springer Publishing Group, United States (2008).

(Continued)

*Primary Examiner* — Amy E Juedes
(74) *Attorney, Agent, or Firm* — Clark & Elbing LLP

(57) ABSTRACT

The present invention contemplates dendritic cell compositions. The dendritic cell compositions employ MHC class-II targeting signals fused to an antigen or fragment thereof to obtain MHC II presentation of the antigen or fragment thereof. In particular, the invention refers to a dendritic cell vaccine comprising dendritic cells expressing a MHC class-II targeting signal fused to an antigen or fragment thereof. Dendritic cell vaccines for the stimulation of an immune response against melanoma-associated antigen are also described.

Figure 1:
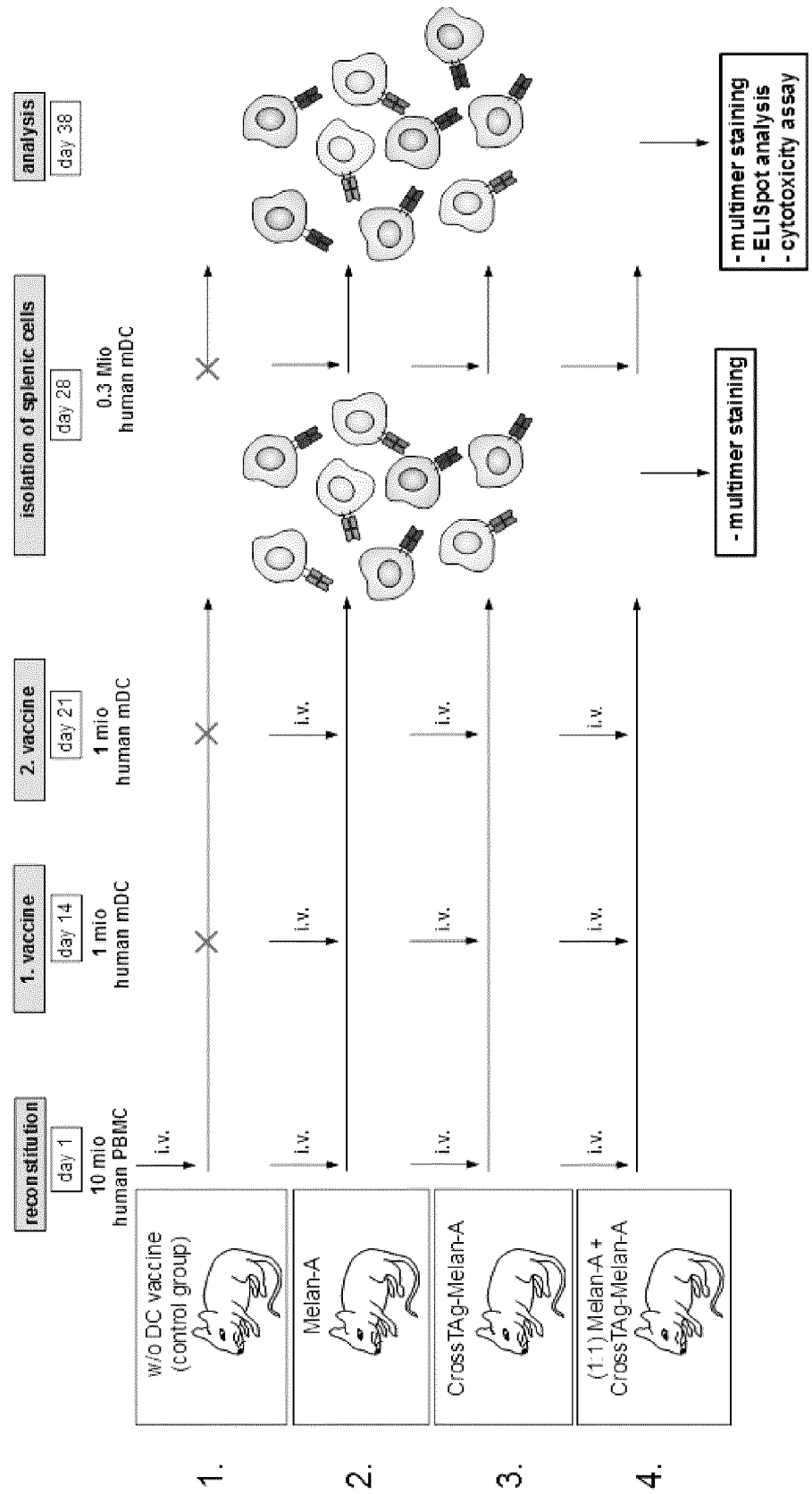

15 Claims, 5 Drawing Sheets
Specification includes a Sequence Listing.

(56) References Cited

FOREIGN PATENT DOCUMENTS

| | | |
|---|---|---|
| EP | 2700708 A2 | 2/2014 |
| JP | H05-504621 | 7/1993 |
| JP | H06502529 | 3/1994 |
| JP | H06-506362 | 7/1994 |
| JP | H07-502165 | 3/1995 |
| JP | H08-502246 | 3/1996 |
| JP | 2007097580 A | 4/2007 |
| JP | 2004535168 A | 11/2014 |
| WO | WO-9107508 | 5/1991 |
| WO | WO-9202629 | 2/1992 |
| WO | WO-9209305 A1 | 6/1992 |
| WO | WO-9305813 | 4/1993 |
| WO | WO-9311161 A1 | 6/1993 |
| WO | WO 9311794 | 6/1993 |
| WO | WO-9404686 A1 | 3/1994 |
| WO | WO-9405801 | 3/1994 |
| WO | WO-9405801 A1 | 3/1994 |
| WO | WO-0155366 A1 | 8/2001 |
| WO | WO-0162908 A2 | 8/2001 |
| WO | WO-0192291 A2 | 12/2001 |
| WO | WO-2004044004 A2 | 5/2004 |
| WO | WO-2005116074 A2 | 12/2005 |
| WO | WO-2005116646 A1 | 12/2005 |
| WO | WO-2007131092 A2 | 11/2007 |
| WO | WO-2011107409 A1 | 9/2011 |
| WO | WO 2013/187906 A1 | 12/2013 |
| WO | WO-2014089335 A2 | 6/2014 |
| WO | WO-2015136072 A1 | 9/2015 |
| WO | WO 2016/057986 A1 | 4/2016 |
| WO | WO-2016193299 A1 | 12/2016 |
| WO | WO-2016193300 A1 | 12/2016 |
| WO | WO-2016193301 A1 | 12/2016 |
| WO | WO-2017109109 A1 | 6/2017 |
| WO | WO-2017109110 A1 | 6/2017 |

OTHER PUBLICATIONS

Wehner, C. et al., "Isolation of antigen-specific CD8+ T lymphocytes in vitro and in vivo," J Immother Cancer 1(suppl):P239, BioMed Central, England (2013).

Zerial, M. et al., "The transmembrane segment of the human transferrin receptor functions as a signal peptide," The EMBO Journal 5: 1543-1550, IRL Press, England (1986).

Van Nuffel, A. et al., "Dendritic Cells Loaded with mRNA encoding full-length tumor antigens prime CD4+ and CD8+ T cells in melanoma patients," Mol Ther 20:1063-1074, Cell Press, United States (2012).

Non-Final Office Action dated Sep. 25, 2019, in U.S. Appl. No. 15/579,117, Schendel, D. et al., filed Dec. 1, 2017, 16 pages.

Anonymous: "Immunomic Therapeutics—3D Animation Script—Final," Aug. 31, 2015, XP055266237, Retrieved from the Internet (URL:http://www.immunomix.com/wp-content/uploads/2015/09/IMMUNOMIX_ARKITEK_V4_Script_FINAL_083115.pdf), retrieved on Apr. 18, 2016.

Arruda, L.B., et al., "Dendritic Cell-lysosomal-associated Membrane Protein (LAMP) and LAMP-1-HIV-1 Gag Chimeras Have Distinct Cellular Trafficking Pathways and Prime T and B Cell Responses to a Diverse Repertoire of Epitopes," Journal of Immunology 177(4):2265-2275, American Association of Immunologists, United States (Aug. 2006).

Becker, C., et al., "Adoptive Tumor Therapy With T Lymphocytes Enriched Through an IFN-gamma Capture Assay," Nature Medicine 7(10):1159-1162, Nature Publishing Company, United States (Oct. 2001).

Burdek, M., et al., "Three-day Dendritic Cells for Vaccine Development: Antigen Uptake, Processing and Presentation," Journal of Translational Medicine 8:90, BioMed Central, England (Sep. 2010).

Wehner, Carina: "Induktion Tumorantigen-spezifischer CD8 + T-Lymphozyten in vitro und in vivo-Dissertation", Jul. 1, 2013 (Jul. 1, 2013). XP55358705, Retrieved from the Internet: URL:https://edoc.ub.uni-muenchen.de/20384/1/Wehner_Carina.pdf [retrieved on Mar. 24, 2017], 177 pages.

Ellinger, C., et al., "MHC Class-II Expression Targeting (CrossTAg) for the Generation of Tumor-Antigen-Specific CD4+ T Lymphocytes," Abstract—CIMT Cancer Immunotherapy Annual Meeting, Mainz, Germany (2013), XP055266213, accessed at https://www.medigene.com/fileadmin/download/abstracts/12_ellinger_-_mhc_class-ii_expression_targeting_crosstag_-cimt_2013.pdf, accessed Nov. 8, 2018.

Engels, B., et al., "Relapse or Eradication of Cancer Is Predicted by Peptide-major Histocompatibility Complex Affinity," Cancer Cell 23(4):516-526, Cell Press, United States (Apr. 2013).

Extended European Search Report for EP Application No. EP15202329, Munich, Germany, dated Aug. 29, 2016, 12 pages.

Frentsch, M., et al., "Direct Access to CD4+ T Cells Specific for Defined Antigens According to CD154 Expression," Nature Medicine 11(10):1118-1124, Nature Publishing Company, United States (2005).

GenBank, "Homo sapiens MAGE family member A4 (MAGEA4), transcript variant 4, mRNA," Accession No. NM_001011550.1, accessed at https://www.ncbi.nlm.nih.gov/nuccore/NM_001011550, accessed on Jun. 23, 2018.

GenBank, "Homo sapiens mRNA for NY-ESO-1 protein," Accession No. AJ003149.1, accessed at https://www.ncbi.nlm.nih.gov/nuccore/AJ003149, accessed on Oct. 7, 2008.

GenBank, "Homo sapiens SSX4 (SSX4) mRNA, complete cds," Accession No. U90841.1, accessed at https://www.ncbi.nlm.nih.gov/nuccore/U90841, accessed on Mar. 18, 1998.

GenBank, "Homo sapiens XAGE-1 mRNA, complete cds," Accession No. AF251237.1, accessed at https://www.ncbi.nlm.nih.gov/nuccore/AF251237, accessed on Aug. 23, 2000.

GenBank, "Human GAGE-1 protein mRNA, complete cds," Accession No. U19142.1, accessed at https://www.ncbi.nlm.nih.gov/nuccore/U19142, accessed on Dec. 4, 1995.

GenBank, "Lysosome-associated membrane glycoprotein 1 precursor," Accession No. NP_005552, accessed at https://www.ncbi.nlm.nih.gov/protein/NP_005552, accessed on Jun. 23, 2018.

GenBank, "Lysosome-associated Membrane Glycoprotein 3 Precursor," Accession No. NP_055213, accessed at https://www.ncbi.nlm.nih.gov/protein/NP_055213.2, accessed on Jun. 11, 2018.

Hinrichs, C.S. and Rosenberg, S.A., "Exploiting the Curative Potential of Adoptive T-cell Therapy for Cancer," Immunological Reviews 257(1):56-71, Blackwell, England (Jan. 2014).

Kavanagh, D.G., et al., "Expansion of HIV-specific CD4+ and CD8+ T Cells by Dendritic Cells Transfected With mRNA Encoding Cytoplasm-or Lysosome-Targeted Nef," Blood 107(5):1963-1969, American Society of Hematology, United States (Mar. 2006).

International Preliminary Report on Patentability for Application No. PCT/EP2016/082445, dated Jun. 26, 2018, 8 pages.

International Search Report and Written Opinion for Application No. PCT/EP2016/082445, dated Apr. 12, 2017, 13 pages.

International Preliminary Report on Patentability for Application No. PCT/EP2016/082443, European Patent Office, Rijswijk, dated Jun. 26, 2018, 9 pages.

International Search Report and Written Opinion for International Application No. PCT/EP2016/082443, European Patent Office, Rijswijk, dated May 23, 2017, 16 pages.

Javorovic, M., et al., "Inhibitory Effect of RNA Pool Complexity on Stimulatory Capacity of RNA-pulsed Dendritic Cells," Journal of immunotherapy 31(1):52-62, Lippincott Williams & Wilkins, United States (Jan. 2008).

Kempkes, B., et al., "Immortalization of Human B Lymphocytes by a Plasmid Containing 71 Kilobase Pairs of Epstein-barr Virus DNA," Journal of Virology 69(1):231-238, American Society for Microbiology, United States (Jan. 1995).

Knabel, M., et al., "Reversible MHC Multimer Staining for Functional Isolation of T-cell Populations and Effective Adoptive Transfer," Nature Medicine 8(6):631-637, Nature Publishing Company, United States (Jun. 2002).

Milosevic, S., et al., "Identification of Major Histocompatibility Complex Class II-restricted Antigens and Epitopes of the Epstein-barr Virus by a Novel Bacterial Expression Cloning Approach,"

(56) References Cited

OTHER PUBLICATIONS

Journal of Virology 80(21):10357-10364, American Society for Microbiology, United States (Nov. 2006).
Moosmann, A., et al., "B Cells Immortalized by a Mini-Epstein-Barr Virus Encoding a Foreign Antigen Efficiently Reactivate Specific Cytotoxic T Cells," Blood 100(5):1755-1764, American Society of Hematology, United States (Sep. 2002).
Mortenson, E.D., et al., "Effective Anti-neu-initiated Antitumor Responses Require the Complex Role of CD4+ T Cells," Clinical Cancer Research, 19(6):1476-1486, The Association, United States (Mar. 2013).
Regn, S., et al., "Ex Vivo Generation of Cytotoxic T Lymphocytes Specific for One or Two Distinct Viruses for the Prophylaxis of Patients Receiving an Allogeneic Bone Marrow Transplant," Bone Marrow Transplantation 27(1):53-64, Nature Publishing Group, England (Jan. 2001).
Schendel, D.J., et al., "Human CD8+ T lymphocytes," in: The Immunology Methods Manual, Lefkovits, Ed, pp. 670-690, 1997.
Schoenbrunn, A., et al., "A Converse 4-1BB and CD40 Ligand Expression Pattern Delineates Activated Regulatory T Cells (Treg) and Conventional T Cells Enabling Direct Isolation of Alloantigen-reactive Natural Foxp3+ Treg," Journal of Immunology 189(12):5985-5994, American Association of Immunologists, United States (Dec. 2012).
Shultz, L.D., et al., "Humanized Mice in Translational Biomedical Research," Nature Reviews Immunology, 7(2):118-130, Nature Publishing Group, England (Feb. 2007).
Spranger, S., et al., "Generation of Th1-Polarizing Dendritic Cells Using the TLR7/8 Agonist CL075," Journal of Immunology, 185(1):738-747, American Association of Immunologists, United States (Jul. 2010).
Spranger, S., et al., "NOD/Scid Il-2rg(Null) Mice: a Preclinical Model System to Evaluate Human Dendritic Cell-based Vaccine Strategies in Vivo," Journal of Translational Medicine, 10:30, BioMed Central, England (Feb. 2012).
Steinle, A., et al., "In Vivo Expansion of HLA-B35 Alloreactive T Cells Sharing Homologous T Cell Receptors: Evidence for Maintenance of an Oligoclonally Dominated Allospecificity by Persistent Stimulation With an Autologous MHC/peptide Complex," The Journal of Experimental Medicine 181(2):503-513, Rockefeller University Press, United States (Feb. 1995).
Su, Z., et al., "Antigen Presenting Cells Transfected With LMP2a Rna Induce CD4+ LMP2a-specific Cytotoxic T Lymphocytes Which Kill via a Fas-independent Mechanism," Leukemia & Lymphoma 43(8):1651-1662, Informa Healthcare, England (Aug. 2002).
Rosenberg, S.A., et al., "Cancer Immunotherapy: Moving Beyond Current Vaccines," Nature Medicine 10(9):909-915, Nature Publishing Company, United States (2004).
Ellinger, Christian: "Gezielte MHC-Klasse-II—Kreuzprasentation fur die Generierung und Isolierung Tumor/Testis—Antigen-spezifischer CD4 + T—Lymphozyten—Dissertation," Jul. 16, 2013 (Jul. 16, 2013). XP55358711, Retrieved from the Internet: URL:https://edoc.ub.uni-muenchen.de/19870/1/Ellinger Christian.pdf, [retrieved-on Mar. 24, 2017], 155 pages.
Wehner, C., et al., "Generation of Tumor Antigen-specific CD4+ and CD8+ T Cells by Simultaneous MHC-I and -II Epitope Presentation in Vitro and in Vivo," Journal for Immunotherapy of Cancer 2 (Suppl 3):P65, BioMed Central, England (2014).
Wilde, S., et al., "Dendritic Cells Pulsed With RNA Encoding Allogeneic MHC and Antigen Induce T Cells With Superior Antitumor Activity and Higher TCR Functional Avidity," Blood 114(10):2131-2139, American Society of Hematology, United States (Sep. 2009).
Wu, T.C., et al., "Engineering an Intracellular Pathway for Major Histocompatibility Complex Class II Presentation of Antigens," Proceedings of the National Academy of Sciences of the United States of America 92(25):11671-11675, National Academy of Sciences, United States (Dec. 1995).
Yu, X., et al., "Antigen-armed Antibodies Targeting B Lymphoma Cells Effectively Activate Antigen-specific CD4+ T Cells," Blood 125(10):1601-1610, American Society of Hematology, United States (Mar. 2015).
Abraham, R.T. and Weiss, A., "Jurkat T Cells and Development of the T-cell Receptor Signalling Paradigm," Nature Reviews. Immunology 4(4):301-308, Nature Pub. Group, England (Apr. 2004).
Ahlgren, K.M., et al., "T Cell Receptor-Vbeta Repertoires in Lung and Blood CD4+ and CD8+ T Cells of Pulmonary Sarcoidosis Patients," BMC Pulmonary Medicine 14(1):50, BioMed Central, England (Mar. 2014).
Altschul, S.F., et al., "Basic Local Alignment Search Tool," Journal of Molecular Biology 215(3):403-410, Elsevier, England (Oct. 1990).
Arbabi Ghahroudi, M., et al., "Selection and Identification of Single Domain Antibody Fragments from Camel Heavy-chain Antibodies," FEBS Letters 414(3):521-526, John Wiley & Sons Ltd., England (Sep. 1997).
Balow, J.P. and Kerase, K.P., "Isolation of Newly Expressed Surface T Cell Antigen Receptor Complexes by Serial Precipitation with Anti-TCR Antibodies and Immobilized Streptavidin," Journal of Immunological Methods 189(2):251-258, Elsevier, Netherlands (Feb. 1996).
Bernett, M.J., et al., "Engineering Fully Human Monoclonal Antibodies from Murine Variable Regions," Journal of Molecular Biology 396(5):1474-1490, Elsevier, England (Mar. 2010).
Bird, R.E., et al., "Single-chain Antigen-binding Proteins," Science 242(4877):423-426, Association for the Advancement of Science, United States (Oct. 1988).
Bonehill A. et al., "Messenger RNA-electroporated dendritic cells presenting MAGE-A3 simultaneously in HLA class I and class II molecules," J Immunol 172(11):6649-6657, The American Association of Immunologists, United States (2004).
Brennan, M., et al., "Preparation of Bispecific Antibodies by Chemical Recombination of Monoclonal Immunoglobulin G1 Fragments," Science 229(4708):81-83, American Association for the Advancement of Science, United States (Jul. 1985).
Brewer, J.L. and Ericson, S.G., "An Improved Methodology to Detect Human T Cell Receptor beta Variable Family Gene Expression Patterns," Journal of Immunological Methods 302(1-2):54-67, Elsevier, Netherlands (Jul. 2005).
Busch, D.H., et al., "Evolution of a Complex T Cell Receptor Repertoire During Primary and Recall Bacterial Infection," The Journal of Experimental Medicine 188(1):61-70, Rockefeller University Press, United States (Jul. 1998).
BV/Hu_TRBVMab.html, last accessed Jul. 9, 2018, 3 pages (2003).
Byers, V.S. and Baldwin, R.W., "Rationale for Clinical Use of Immunotoxins in Cancer and Autoimmune Disease," Seminars in Cell Biology 2(1):59-70, Academic Press, England (Feb. 1991).
Call, M.E. and Wucherpfennig, K.W., "The T Cell Receptor: Critical Role of the Membrane Environment in Receptor Assembly and Function," Annual Review of Immunology 23:101-125, Annual Reviews Inc., United States (2005).
Chiocchia, G., et al., "Therapy against murine collagen-induced arthritis with T cell receptor $V_\beta$-specific antibodies*," Eur. J. Immunol. 21:2899-2905, Wiley-VCH, Germany (1991).
Chu, T.H. et al., "Highly Efficient Eukaryotic Gene Expression vectors for Peptide Secretion," Biotechniques Pept Res 8:101-7, Future Science Group, England, (1995).
Cohen, C.J., et al., "Enhanced Antitumor Activity of T Cells Engineered to Express T-cell Receptors with a Second Disulfide Bond," Cancer Research 67(8):3898-3903, American Association for Cancer Research, United States (Apr. 2007).
Cohen, C.J., et al., "Enhanced Antitumor Activity of Murine-human Hybrid T-cell Receptor (TCR) in Human Lymphocytes is Associated with Improved Pairing and TCR/CD3 Stability," Cancer Research 66(17):8878-8886, American Association for Cancer Research, United States (Sep. 2006).
Conrath, K.E., et al., "Beta-lactamase Inhibitors Derived From Single-domain Antibody Fragments Elicited in the Camelidae," Antimicrobial Agents and Chemotherapy 45(10):2807-2812, American Society for Microbiology, United States (Oct. 2001).

(56) References Cited

OTHER PUBLICATIONS

Coren, L., et al., "Production of Retroviral constructs for effective transfer and expression of T-cell receptor genes using Golden Gate Cloning," Biotechniques 58(3):135-139, Future Medicine, United States (Mar. 2015).
Cortez-Retamozo, V., et al., "Efficient Cancer Therapy with a Nanobody-based Conjugate," Cancer Research 64(8):2853-2857, American Association for Cancer Research, United States (Apr. 2004).
De Alboran, I.M., et al., "Attenuation of autoimmune disease and lymphocyte accumulation in MRL//pr mice by treatment with anti-$V_\beta$ antibodies*," Eur. J. Immunol. 22:2153-2158, Wiley-VCH, Germany (Apr. 1992).
Delobel, A., et al., "Therapeutic Antibody Glycosylation Analysis: a Contract Research Organization Perspective in the Frame of Batch Release or Comparability Support," Methods in Molecular Biology 988:115-143, Humana Press, United States (2013).
Desmet, J., et al., Chapter 22—"Humanization by Resurfacing," in Antibody Engineering, vol. 1, second edition, Kontermann, R, and Dubel, S., eds., pp. 341-342, Springer-Verlag Berlin Heidelberg, Germany (2010).
Desmyter, A., et al., "Antigen Specificity and High Affinity Binding Provided by One Single Loop of a Camel Single-domain Antibody," The Journal of Biological Chemistry 276(28):26285-26290, American Society for Biochemistry and Molecular Biology, United States (Jul. 2001).
Diener, E., et al., "Specific Immunosuppression by Immunotoxins Containing Daunomycin," Science 231(4734):148-150, American Association for the Advancement of Science, United States (Jan. 1986).
Dreyer, A.M., et al., "An efficient system to generate monoclonal antibodies against membrane-associated proteins by immunization with antigen-expressing mammalian cells," BMC Technology 10:87, Bio Med Central, England (2010).
Fanger, M.W., et al., "Bispecific Antibodies and Targeted Cellular Cytotoxicity," Immunology Today 12(2):51-54, Elsevier Science Publishers, England (Feb. 1991).
Fanger, M.W., et al., "Bispecific Antibodies," Critical Reviews in Immunology 12(3-4):101-24, Begell House, United States (1992).
Fanger, M.W., et al., "Use of Bispecific Antibodies in the Therapy of Tumors," in Immunoconjugate Therapy of Hematologic Malignancies, Chapter 10, Rosen, S., ed., pp. 181-194, Springer US, United States (1991).
Folch, G. and Lefranc, M.P., "The Human T Cell Receptor Beta Variable (TRBV) Genes," Experimental and Clinical Immunogenetics 17(1):42-54, Karger, Switzerland (2000).
Greenberg, A.S., et al., "A New Antigen Receptor Gene Family that Undergoes Rearrangement and Extensive Somatic Diversification in Sharks," Nature 374(6518):168-173, Nature Publishing Group, England (Mar. 1995).
Gruber, M., et al., "Efficient Tumor Cell Lysis Mediated by a Bispecific Single Chain Antibody Expressed in Escherichia coli," The Journal of Immunology 152(11):5368-5374, The American Association of Immunologists, Inc., United States (1994).
Hamers-Casterman, C., et al., "Naturally Occurring Antibodies Devoid of Light Chains," Nature 363(6428):446-448, Nature Publishing Group, England (Jun. 1993).
Harlow, et al. (Eds), Antibodies a Laboratory Manual, Cold Spring Harbor Laboratory, Chapter 6, NY (1988).
Higgins, P.J., et al., "In Vitro Inhibition of a Variety of Human Immunodeficiency Virus Isolates by a Broadly Reactive, V3-directed Heteroconjugate Antibody In Vitro Inhibition of a Variety of Human Immunodeficiency Virus Isolates by a Broadly Reactive, V3-directed Heteroconjugate Antibody," The Journal of Infectious Diseases 166(1):198-202, Oxford University Press, United States (Jul. 1992).
Hildinger, M., et al., "Design of 5' Untranslated Sequences in Retroviral Vectors Developed for Medical Use," Journal of Virology 73(5):4083-4089, American Society for Microbiology, United States (May 1999).
Hirsch, T., et al., "Effects of In Vivo Administration of anti-T3 Monoclonal Antibody on T cell Function in Mice—I. Immunosuppression of transplantation responses," Journal of Immunology 140(11): 3766-3772, American Association of Immunologists, United States (1988).
Holliger, P., et al., "Diabodies: Small Bivalent and Bispecific Antibody Fragments," Proceedings of the National Academy of Sciences USA 90(14):6444-6448, National Academy of Sciences, United States (Jul. 1993).
Huston, J.S., et al., "Protein Engineering of Antibody Binding Sites: Recovery of Specific Activity in an Anti-digoxin Single-chain Fv Analogue Produced in Escherichia coli," Proceedings of the National Academy of Sciences USA 85(16):5879-5883, National Academy of Sciences, United States (Aug. 1988).
IMGT Repertoire (IG and TR) IGMT Web Resources, "Reagents monoclonal antibodies: anti-mouse TRAV," accessed at http://www.imgt.org/IMGTrepertoire/index.php?section=Regulation&repertoire=antibodies&species=mouse&group=TRAV.
IMGT Repertoire (IG and TR), "Reagents monoclonal antibodies: anti-mouse TRBV," accessed at http://www.imgt.org/IMGTrepertoire/index.php?section=Regulation&repert.
IMGT Repertoire (IG and TR), IGMT Web Resources, "Reagents Monoclonal antibodies: anti-human TRBV," accessed at http://www.imgt.org/IMGTrepertoire/Regulation/antibodies/human/TRB/TR.
International Search Report and Written Opinion for International Application No. PCT/EP2016/062366, European Patent Office, Rijswijk, dated Aug. 31, 2016, 17 pages.
International Search Report and Written Opinion for International Application No. PCT/EP2016/062367, European Patent Office, Rijswijk, dated Aug. 2, 2016, 14 pages.
International Search Report and Written Opinion for International Application No. PCT/EP2016/062370, European Patent Office, Rijswijk, dated Jul. 8, 2016, 12 pages.
IOTest Beta Mark, "25 T-Cell Repertoire assays," IOTest® Beta Mark PN IM3497 TCR Vβ Repertoire Kit, accessed at https://www.bccytometry.com/PDF/DataSheet/IM3497DS.pdf, last accessed Jun. 20, 2007, 20 pages.
Irving, R.A., et al., "Ribosome Display and Affinity Maturation: From Antibodies to Single V-domains and Steps Towards Cancer Therapeutics," Journal of Immunological Methods 248(1-2):31-45, Elsevier Science Publishers, Netherlands (Feb. 2001).
Karlin, S. and Altschul, S.F., "Applications and Statistics for Multiple High-Scoring Segments in Molecular Sequences," Proceedings of the National Academy of Sciences of the United States of America 90(12):5873-5877, National Academy of Sciences, United States (Jun. 1993).
Kessels, H.W.H.G., et al., "Changing T Cell Specificity by Retroviral T Cell Receptor Display," Proceedings of the National Academy of Sciences of the United States of America 97(26):14578-14583, National Academy of Sciences, United States (Dec. 2000).
Kipriyanov, S.M., et al., "Recombinant Single-chain Fv Fragments Carrying C-terminal Cysteine Residues: Production of Bivalent and Biotinylated Miniantibodies," Molecular Immunology 31(14):1047-1058, Pergamon Press, England (1994).
Kipriyanov, S.M., et al., "Single-chain Antibody Streptavidin Fusions: Tetrameric Bifunctional Scfv-complexes With Biotin Binding Activity and Enhanced Affinity to Antigen," Human Antibodies and Hybridomas 6(3):93-101, Butterworth-Heinemann, United States (1995).
Kohler, G. and Milstein, C., "Continuous Cultures of Fused Cells Secreting Antibody of Predefined Specificity," Nature 256(5517):495-497, Macmillan Journals Ltd., England (Aug. 1975).
Kontermann, "Dual targeting strategies with bispecific antibodies," mAbs 4(2):182-197, Taylor & Francis, England (2012).
Lee, N.E. and Davis, M.M., "T Cell Receptor beta-chain Genes in BW5147 and Other AKR Tumors. Deletion Order of Murine V beta Gene Segments and Possible 5' Regulatory Regions," Journal of Immunology 140(5):1665-1675, American Association of Immunologists, United States (Mar. 1988).
Lefranc, M.P., et al., "IMGT Unique Numbering for Immunoglobulin and T Cell Receptor Variable Domains and Ig Superfamily V-like Domains," Developmental and Comparative Immunology 27(1):55-77, Elsevier Science, United States (Jan. 2003).

(56) References Cited

OTHER PUBLICATIONS

Lefranc, M.P., et al., "IMGT, the International ImMunoGeneTics Information System," Nucleic Acids Research 33:D593-D597, Oxford University Press, England (Jan. 2005).
Letourneur, F. and Malissen, B., "Derivation of a T Cell Hybridoma Variant Deprived of Functional T Cell Receptor alpha and beta Chain Transcripts Reveals a Nonfunctional alpha-mRNA of BW5147 Origin," European Journal of Immunology 19(12):2269-2274, Wiley-VCH, Germany (Dec. 1989).
Lu, J., et al., "Analysis of T-cell Repertoire in Hepatitis-associated Aplastic Anemia," Blood 103(12):4588-4593, American Society of Hematology, United States (Jun. 2004).
Maeda, T., et al., "Amelioration of Acute Graft-Versus-Host Disease and Re-Establishment of Tolerance by Short-Term Treatment With an Anti-TCR Antibody," Journal of Immunology 153(9):4311-4320, American Association of Immunologists, United States (Nov. 1994).
Mamedov, I.Z., et al., "Preparing Unbiased T-Cell Receptor and Antibody cDNA Libraries for the Deep Next Generation Sequencing Profiling," Frontiers in Immunology 4:456, Frontiers Research Foundation, Switzerland (2013).
Milstein, C. and Cuello, A.C., "Hybrid Hybridomas and their Use in Immunohistochemistry," Nature 305(5934):537-540, Nature Publishing Group, England (Oct. 1983).
Muyldermans, S. and Lauwereys, M., "Unique Single-Domain Antigen Binding Fragments Derived From Naturally Occurring Camel Heavy-Chain Antibodies," Journal of Molecular Recognition 12(2):131-140, John Wiley & Sons, England (Mar.-Apr. 1999).
Muyldermans, S., "Single Domain Camel Antibodies: Current Status," Reviews in Molecular Biotechnology 74(4):277-302, Elsevier Science Publishers, Netherlands (2001).
Nguyen, V.K., et al., "Functional Heavy-Chain Antibodies in Camelidae," Advances in Immunology 79:261-296, Academic Press, United States (2001).
Nguyen, V.K., et al., "Heavy-Chain Antibodies in Camelidae; a Case of Evolutionary Innovation," Immunogenetics 54(1):39-47, Springer Verlag, United States (Apr. 2002).
Nguyen, V.K., et al., "Loss of Splice Consensus Signal Is Responsible for the Removal of the Entire C(H)1 Domain of the Functional Camel IGG2A Heavy-Chain Antibodies," Molecular Immunology 36(8):515-524, Pergamon Press, England (Jun. 1999).
Nguyen, V.K., et al., "The Specific Variable Domain of Camel Heavy-chain Antibodies Is Encoded in the Germline," Journal of Molecular Biology 275(3):413-418, Elsevier, England (Jan. 1998).
Nuttall, S.D., et al., "Isolation of the New Antigen Receptor From Wobbegong Sharks, and Use as a Scaffold for the Display of Protein Loop Libraries," Molecular Immunology 38(4):313-326, Pergamon Press, England (Aug. 2001).
Office Action for Japanese Application No. JP2017-563246, dated Dec. 11, 2018, The Japan Patent Office, Tokyo, Japan, 6 pages.
Office Action for Japanese Application No. JP2017-563247, dated Dec. 11, 2018, The Japan Patent Office, Tokyo, Japan, 6 pages.
Office Action for New Zealand Patent IP No. 737400, dated Sep. 3, 2018, New Zealand Intellectual Property Office, New Zealand, 7 pages.
Office Action for New Zealand Patent IP No. 737423, dated Aug. 2, 2018, New Zealand Intellectual Property Office, New Zealand, 6 pages.
Office Action for New Zealand Patent IP No. 737851, dated Aug. 16, 2018, New Zealand Intellectual Property Office, New Zealand, 6 pages.
IMGT Repertoire (IG and TR), "Reagents monoclonal antibodies: anti-mouse TRBV," accessed at http://www.imgt.org/IMGTrepertoire/index.php?section=Regulation&repertoire=antibodies&species=mouse&group=TRBV, last accessed Jul. 9, 2018, 2 pages (2011).
Olsson, T., et al., "Depletion of Vβ5.2/5.3 T cells with a humanized antibody in patients with multiple sclerosis," European Journal of Neurology 9:153-164, Wiley Blackwell, United States (2002).
Penaranda, C., et al., "Anti-CD3 Therapy Promotes Tolerance by Selectively Depleting Pathogenic Cells While Preserving Regulatory T cells," Journal of Immunology 187(4):2015-2022, The American Association of Immunologists, United States (2011).
Pilch, H., et al., "Improved Assessment of T-cell Receptor (TCR) VB Repertoire in Clinical Specimens: Combination of TCR-CDR3 Spectratyping With Flow Cytometry-based TCR VB Frequency Analysis," Clinical and Diagnostic Laboratory Immunology 9(2):257-266, American Society for Microbiology, United States (Mar. 2002).
Poljak, R.J., "Production and Structure of Diabodies," Structure 2(12):1121-1123, Cell Press, United States (1994).
RecName: Full=Lysosome-associated membrane glycoprotein 3; (LAMP-3),UniprotAC:Q9UQV4 (LAMP3_HUMAN), Nov. 11, 2015, <URL: https://www.uniprot.org/uniprot/09UQV4.txt?version=101>.
RecName: Full=Lysosome-associated membrane glycoprotein 1, Uniprot AC:P11279 (LAMP1_HUMAN), Dec. 9, 2015, <URL: https://www.uniprot.org/uniprot/P 11279. txt?version= 155>.
Riechmann, L. and Muyldermans, S., "Single Domain Antibodies: Comparison of Camel VH and Camelised Human VH Domains," Journal of Immunological Methods 231(1-2):25-38, Elsevier, Netherlands (Dec. 1999).
Roux, K.H., et al., "Structural Analysis of the Nurse Shark (New) Antigen Receptor (NAR): Molecular Convergence of NAR and Unusual Mammalian Immunoglobulins," Proceedings of the National Academy of Sciences of the United States of America 95(20):11804-11809, National Academy of Sciences, United States (Sep. 1998).
Schambach, A., et al., "Context Dependence of Different Modules for Posttranscriptional Enhancement of Gene Expression From Retroviral Vectors," Molecular Therapy 2(5):435-445, Cell Press, United States (Nov. 2000).
Shevach, E.M., Current Protocols in Immunology, Chapter 13 Complement, pp. 13.0.1-13.0.4, Jun. 2005.
Sommermeyer, D. and Uckert, W., "Minimal Amino Acid Exchange in Human TCR Constant Regions Fosters Improved Function of TCR Gene-Modified T Cells," Journal of Immunology 184(11):6223-6231, American Association of Immunologists, United States (Jun. 2010).
Su, C., et al., "Evolutionary Dynamics of the T-Cell Receptor VB Gene Family as Inferred from the Human and Mouse Genomic Sequences," Molecular Biology and Evolution 18(4):503-513, Oxford Academic, England (2001).
Traunecker, A., et al., "Janusin: New Molecular Design for Bispecific Reagents," International Journal of Cancer 7:51-52, Alan R. Liss, Inc., United States (1992).
Urlaub, G. and Chasin, L.A., "Isolation of Chinese Hamster Cell Mutants Deficient in Dihydrofolate Reductase Activity," Proceedings of the National Academy of Sciences USA 77(7):4216-4220, National Academy of Sciences, United States (Jul. 1980).
Van Der Linden, R.H., et al., "Improved Production and Function of Llama Heavy Chain Antibody Fragments by Molecular Evolution," Journal of Biotechnology 80(3):261-270, Elsevier Science Publishers, Netherlands (Jul. 2000).
Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).
Woolven, B.P., et al., "The Structure of the Llama Heavy Chain Constant Genes Reveals a Mechanism for Heavy-chain Antibody Formation," Immunogenetics 50(1-2):98-101, Springer Verlag, United States (Oct. 1999).
Zumla, et al., "Use of a Murine T-Cell Hybridoma Expressing Human T-Cell Receptor alpha and beta Products as a tool for the production of Human T-Cell Receptor-Specific Monoclonal Antibodies," Human Immunology 35(3):141-148, American Society for Histocompatibility and Immunogenetics, United States (1992).
Boullart; A.C.I. et al., "Maturation of monocyte-derived dendritic cells with Toll-like receptor 3 and 7/8 ligands combined with prostaglandin E2 results in high interleukin-12 production and cell migration," *Cancer Immunol Immunother* 57:1589-97, Springer Publishing Group, United States (2008).

\* cited by examiner

A)

B)

C)

A)

B)

SEQUENCE LISTING

<160> NUMBER OF SEQ ID NOS: 14

<210> SEQ ID NO 1
<211> LENGTH: 28
<212> TYPE: PRT
<213> ORGANISM: Homo sapiens

<400> SEQUENCE: 1

Met Ala Ala Pro Gly Ser Ala Arg Arg Pro Leu Leu Leu Leu Leu Leu
1               5                   10                  15

Leu Leu Leu Leu Gly Leu Met His Cys Ala Ser Ala
            20                  25

<210> SEQ ID NO 2
<211> LENGTH: 29
<212> TYPE: PRT
<213> ORGANISM: Homo sapiens

<400> SEQUENCE: 2

Met Ala Ala Pro Gly Ser Ala Arg Arg Pro Leu Leu Leu Leu Leu
1               5                   10                  15

Leu Leu Leu Leu Gly Leu Met His Cys Ala Ser Ala Ala
            20                  25

<210> SEQ ID NO 3
<211> LENGTH: 40
<212> TYPE: PRT
<213> ORGANISM: Homo sapiens

<400> SEQUENCE: 3

Ser Ser Asp Tyr Thr Ile Val Leu Pro Val Ile Gly Ala Ile Val Val
1               5                   10                  15

Gly Leu Cys Leu Met Gly Met Gly Val Tyr Lys Ile Arg Leu Arg Cys
            20                  25                  30

Gln Ser Ser Gly Tyr Gln Arg Ile
        35                  40

<210> SEQ ID NO 4
<211> LENGTH: 4
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any hydrophobic amino acid

<400> SEQUENCE: 4

Tyr Xaa Xaa Xaa
1

<210> SEQ ID NO 5
<211> LENGTH: 4
<212> TYPE: PRT
<213> ORGANISM: Homo sapiens

<400> SEQUENCE: 5

Tyr Gln Arg Ile
1

<210> SEQ ID NO 6
<211> LENGTH: 28
<212> TYPE: PRT
<213> ORGANISM: Homo sapiens

<400> SEQUENCE: 6

Met Val Cys Phe Arg Leu Phe Pro Val Pro Gly Ser Gly Leu Val Leu
1               5                   10                  15

```
Val Cys Leu Val Leu Gly Ala Val Arg Ser Tyr Ala
            20                  25
```

```
<210> SEQ ID NO 7
<211> LENGTH: 29
<212> TYPE: PRT
<213> ORGANISM: Homo sapiens

<400> SEQUENCE: 7

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu
            20                  25
```

```
<210> SEQ ID NO 8
<211> LENGTH: 27
<212> TYPE: PRT
<213> ORGANISM: Homo sapiens

<400> SEQUENCE: 8

Met Pro Arg Gln Leu Ser Ala Ala Ala Leu Phe Ala Ser Leu Ala
1               5                   10                  15

Val Ile Leu His Asp Gly Ser Gln Met Arg Ala
            20                  25
```

```
<210> SEQ ID NO 9
<211> LENGTH: 28
<212> TYPE: PRT
<213> ORGANISM: Homo sapiens

<400> SEQUENCE: 9

Met Pro Arg Gln Leu Ser Ala Ala Ala Leu Phe Ala Ser Leu Ala
1               5                   10                  15

Val Ile Leu His Asp Gly Ser Gln Met Arg Ala Lys
            20                  25
```

```
<210> SEQ ID NO 10
<211> LENGTH: 21
<212> TYPE: PRT
<213> ORGANISM: Homo sapiens

<400> SEQUENCE: 10

Met Arg Leu Ala Val Leu Phe Ser Gly Ala Leu Leu Gly Leu Leu Ala
1               5                   10                  15

Ala Gln Gly Thr Gly
            20
```

```
<210> SEQ ID NO 11
<211> LENGTH: 22
<212> TYPE: PRT
<213> ORGANISM: Homo sapiens

<400> SEQUENCE: 11

Met Arg Leu Ala Val Leu Phe Ser Gly Ala Leu Leu Gly Leu Leu Ala
1               5                   10                  15

Ala Gln Gly Thr Gly Asn
            20
```

```
<210> SEQ ID NO 12
<211> LENGTH: 17
<212> TYPE: PRT
<213> ORGANISM: Homo sapiens
```

```
<400> SEQUENCE: 12

Met Leu Leu Leu Pro Phe Gln Leu Leu Ala Val Leu Phe Pro Gly Gly
1               5                   10                  15

Asn

<210> SEQ ID NO 13
<211> LENGTH: 18
<212> TYPE: PRT
<213> ORGANISM: Homo sapiens

<400> SEQUENCE: 13

Met Leu Leu Leu Pro Phe Gln Leu Leu Ala Val Leu Phe Pro Gly Gly
1               5                   10                  15

Asn Ser

<210> SEQ ID NO 14
<211> LENGTH: 42
<212> TYPE: PRT
<213> ORGANISM: Homo sapiens

<400> SEQUENCE: 14

Asp Pro Ser Ser Asp Tyr Thr Ile Val Leu Pro Val Ile Gly Ala Ile
1               5                   10                  15

Val Val Gly Leu Cys Leu Met Gly Met Gly Val Tyr Lys Ile Arg Leu
            20                  25                  30

Arg Cys Gln Ser Ser Gly Tyr Gln Arg Ile
        35                  40
```

DENDRITIC CELL COMPOSITION

FIELD OF THE INVENTION

The present invention contemplates dendritic cell compositions. The dendritic cell compositions employ MHC class-II targeting signals fused to an antigen or fragment thereof to obtain MHC II presentation of the antigen or fragment thereof.

In particular, the invention refers to a dendritic cell vaccine comprising dendritic cells expressing a MHC class-II targeting signal fused to an antigen or fragment thereof. Dendritic cell vaccines for the stimulation of an immune response against melanoma-associated antigen are also described.

BACKGROUND OF THE INVENTION

Dendritic cells represent a very potent agent in immune therapy because they can efficiently prime naive T cells during development of T cell-mediated immunity and stimulate adaptive immune responses. Dendritic cells have the ability to activate immune responses not only against pathogens, but also against malignant cells. In vivo, immature- or intermediate-stage dendritic cells patrol peripheral tissues to capture and process antigens. Under the influence of local cytokines and danger signals, dendritic cells undergo complex maturation processes and migrate to regional lymph nodes, where they form immunological synapses with T cells and present peptides derived from collected antigens in context with MHC class-I or -II molecules. CD4+ T cell activation is dependent on MHC-II complex binding, while CD8+ interaction is dependent on MHC I binding.

The dendritic cell licensing model describes an indirect CD4+ T cell help for CD8+ T cells by interaction mediated activation that enables dendritic cells to provide costimulatory signals. Thus, for an efficient immune response against tumors, CD4+ T cell help has acquired an essential role as more and more is known about their important role for the expansion and memory generation of antigen-specific CD8+ T cells. Moreover, as tumor-antigens are mostly self-antigens which do not provide a "danger signal" like pathogenic antigens (e.g. PAMPs: pathogen-associated molecular patterns) the CD4+ T cell help is crucial for the induction of a CD8+ T cell memory.

As a consequence, improved dendritic cell vaccines that facilitate that the immune system of a patient can attack his own tumor cells and build long-lasting immunity are needed. It is desired that the vaccine induces higher proliferation of T cells, enhanced activation induced IFN γ secretion of T cells and higher tumor killing capacity of T cells.

OBJECTIVES AND SUMMARY OF THE INVENTION

Therefore, it is an objective of the invention to provide an advanced dendritic cell vaccine that allows the presentation of the antigen on the MHC II complex.

Therefore, a first aspect of the invention contemplates a dendritic cell composition comprising dendritic cells expressing at least one fusion protein comprising
 at least one antigen or a fragment thereof,
 an endoplasmatic reticulum (ER)-translocation signal sequence preceding the N-terminus of the antigen, and
 a transmembrane and cytoplasmic domain comprising an endosomal/lysosomal targeting sequence following the C-terminus of the antigen.

Further, the additional stimulation of antigen-specific CD8+ T cells for an improved immune response is desired.

Thus, in a preferred embodiment the dendritic cell composition further comprises dendritic cells expressing at least one antigen or a fragment thereof wherein the antigen is not fused to a targeting signal sequence that promotes the MHC II presentation of the antigen or fragment thereof.

Typically, the targeting signal sequence that promotes the MHC II presentation is at least one selected from the group consisting of
 an endoplasmatic reticulum (ER)-translocation signal sequence preceding the N-terminus of the antigen, and
 a transmembrane and cytoplasmic domain comprising an endosomal/lysosomal targeting sequence following the C-terminus of the antigen.

Usually, the fusion protein and the antigen (which is not fused to a targeting signal sequence) are transiently or stably expressed, preferably stably expressed. For example, the transient expression may be carried out by introducing ivt-RNA.

In some embodiments, the endosomal/lysosomal targeting sequence is derived from DC-LAMP. Preferably, the endosomal/lysosomal targeting sequence is human. One embodiment refers to a dendritic cell composition as described herein, wherein the endosomal/lysosomal targeting sequence comprises the sequence SEQ ID NO: 3 or a fragment thereof. In a specific embodiment, the endosomal/lysosomal targeting sequence comprises the sequence SEQ ID NO: 14 or a fragment thereof.

The ER translocation signal sequence may be derived from an endosomal/lysosomal associated protein. Preferably, the ER translocation signal sequence is derived from LAMP1. More preferably the ER translocation signal sequence comprises the sequence SEQ ID NO: 1 or a fragment thereof.

In some embodiments, the dendritic cells are mature dendritic cells generated by a method comprising the following steps:
 (i) provision of monocytes;
 (ii) incubation of the monocytes of step i) with IL-4 and GM-CSF;
 (iii) incubation of the monocytes of step ii) with IL-4 and GM-CSF in combination with a maturation cocktail.

For example, the maturation cocktail comprises a combination of IL-ß, TNF-α, IFN-γ, TLR7/8 agonist, PGE2 and TLR3 agonist. The incubation of step ii) may last at least 2 days. The incubation of step iii) may last at least 12 hours, preferably 24 hours. Preferably the TLR7/8 agonist is R848 and the TLR3 agonist is poly(I:C).

In specific embodiments the antigen is MELAN-A.

Another aspect of the invention refers to a dendritic cell vaccine comprising the dendritic cell composition as described herein. Preferably, the dendritic cells are autologous cells.

Typically, the dendritic cell composition and the dendritic cell vaccine are pharmaceutically acceptable fluid compositions.

Another aspect of the invention refers to a dendritic cell composition according to the invention or dendritic cell vaccine according to the invention for use as a medicament.

One embodiment of the invention relates to a dendritic cell vaccine as described herein for use in the treatment of cancer.

Specific embodiments refer to a dendritic cell composition or dendritic cell vaccine according to the invention for use in stimulating an immune response against a melanoma-associated antigen. In a specific embodiment, the melanoma-associated antigen is MELAN-A.

FIGURE LEGENDS

FIG. 1: Experimental overview of the vaccination procedure.

On day one, 16 mice divided into four different groups were engrafted each with 10×106 million human PBMC from a healthy HLA-A*02:01-positive donor. The peripheral T cell repertoire was reconstituted within the following 14 days. Vaccination was applied on day 14 and on day 21, administering 1×10$^6$ mature dendritic cells transfected with either conventional ivt-RNA (2) or CrossTAg-ivt-RNA (3). In addition, one group received a 1:1 mixture of mature dendritic cells transfected with either CrossTAg- or conventional ivt-RNA (4). The control group was not vaccinated (1). On day 28, splenic cells were isolated and screened for Melan-A specific CD8+ T cells by multimer staining using an HLA-A*02:01-Melan-A-specific multimer. Remaining splenic cells were restimulated in vitro with appropriate dendritic cells and expanded for another 10 days. Splenic cells isolated from the control group received only human IL-2 for further in vitro cultivation. Quantification of Melan-A specific CD8+ T cells and functionality tests, like IFN-γ-secretion assays and cytotoxicity assays, were conducted on day 38.

Figure 2:
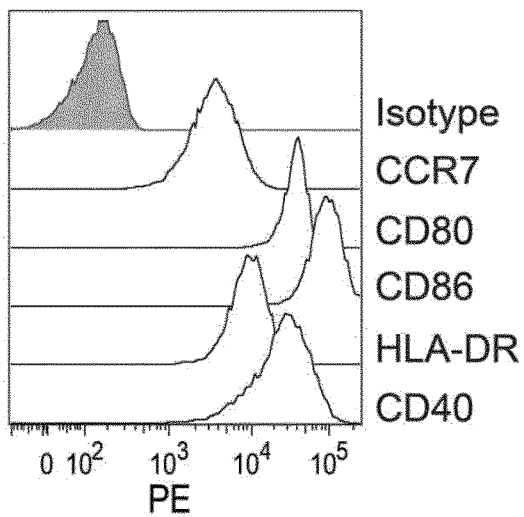
Figure 2:
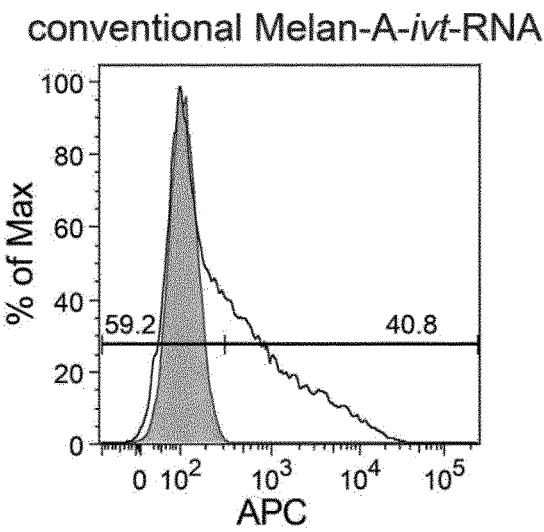
Figure 2:
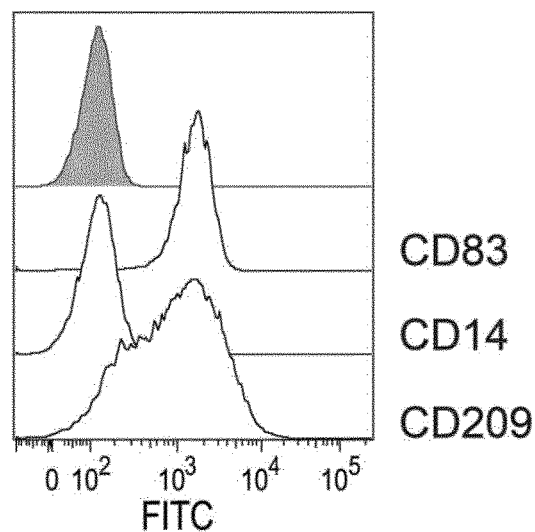
Figure 2:
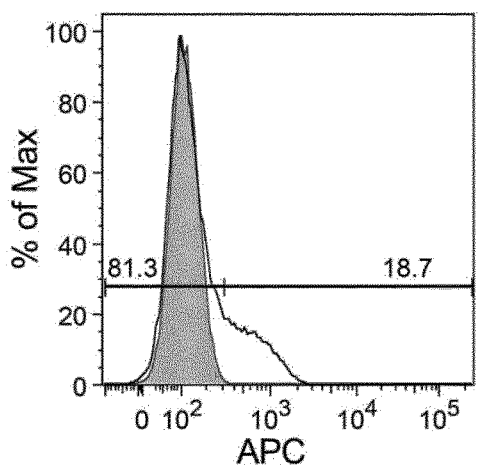

FIG. 2: Maturation and electroporation of dendritic cells.

Mature dendritic cells used for vaccination on day 14 (1. vaccination) and day 21 (2. vaccination) were generated by isolation of monocytes from a healthy HLA-A*02:01 blood donor which were then matured following the 3d DC protocol comprising IL-ß, TNF-α, IFN-γ, the TLR7/8 agonist R848, PGE2 and TLR3. (A) To verify the maturation status, dendritic cells were stained with monoclonal antibodies binding to different surface markers specific for either mature (CD80, CD83, CD86, CD40, CCR7, CD209 and HLA-DR) or immature (CD14) cells and analyzed by FACS analysis. Isotype control antibodies served as a negative control. (B) Prior to administration, mature dendritic cells were transfected with either CrossTAg-Melan-A- or conventional Melan-A-ivt-RNA. After 6 hours of incubation, Melan-A expression was validated by intracellular staining (APC) of Melan-A protein.

Figure 3:
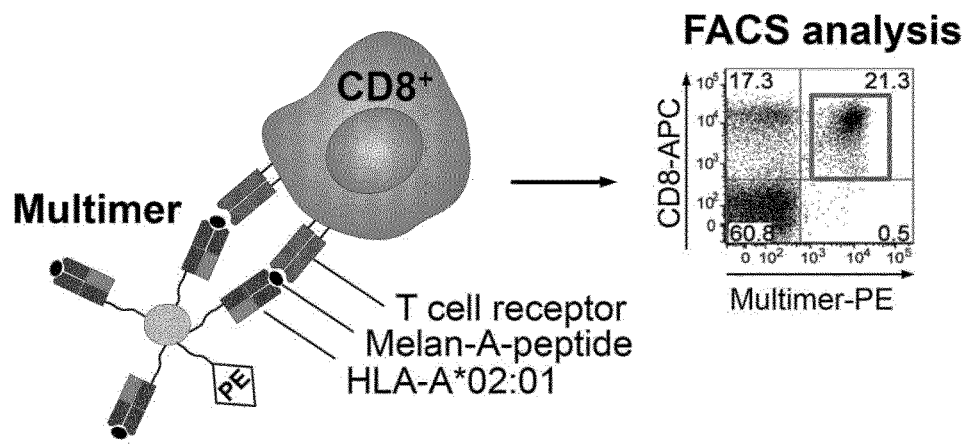
Figure 3:
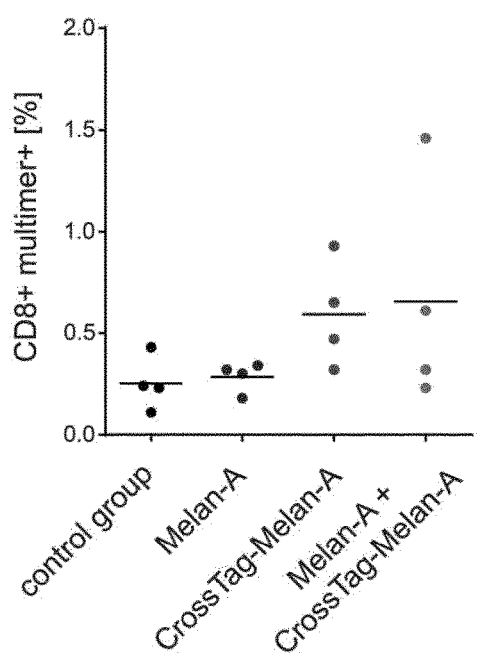
Figure 3:
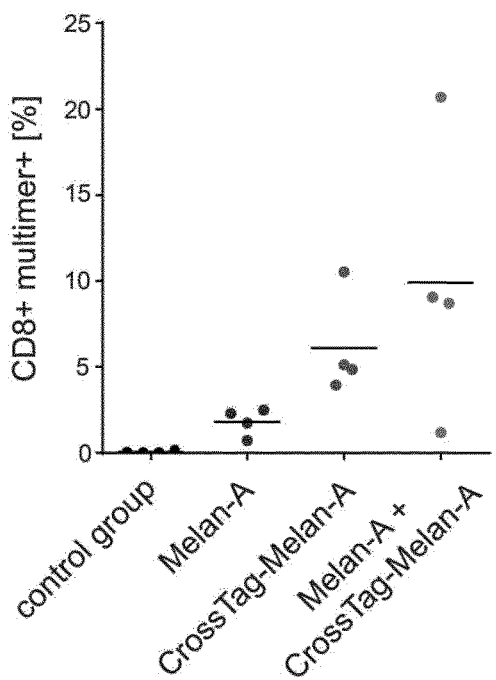

FIG. 3: Multimer-staining of isolated in vitro expanded splenocytes.

(A) Schematic illustration of multimer-stainings: MHC-molecules (HLA-A*02:01) are interlinked and labeled by a fluorescence marker (phycoerythrine, PE). For comparison of induction efficiency of different DC vaccines, CD8- and multimer-double positive cells were taken into account. Number of Melan-A specific CD8+ T cells in splenic populations was measured (B) ex vivo and after (C) in vitro expansion for another 10 days with corresponding dendritic cells and IL-2 (control group was only treated with IL-2). Cells were stained with HLA-A*02:01-Melan-A-multimer and monoclonal antibodies for CD8. Each graph summarizes percentage of Melan-A specific CD8+ T cells from each NSG recipient in an exemplary experiment. Analyzed were 3 individual experiments with a total of 16 mice per experiment.

Figure 4:
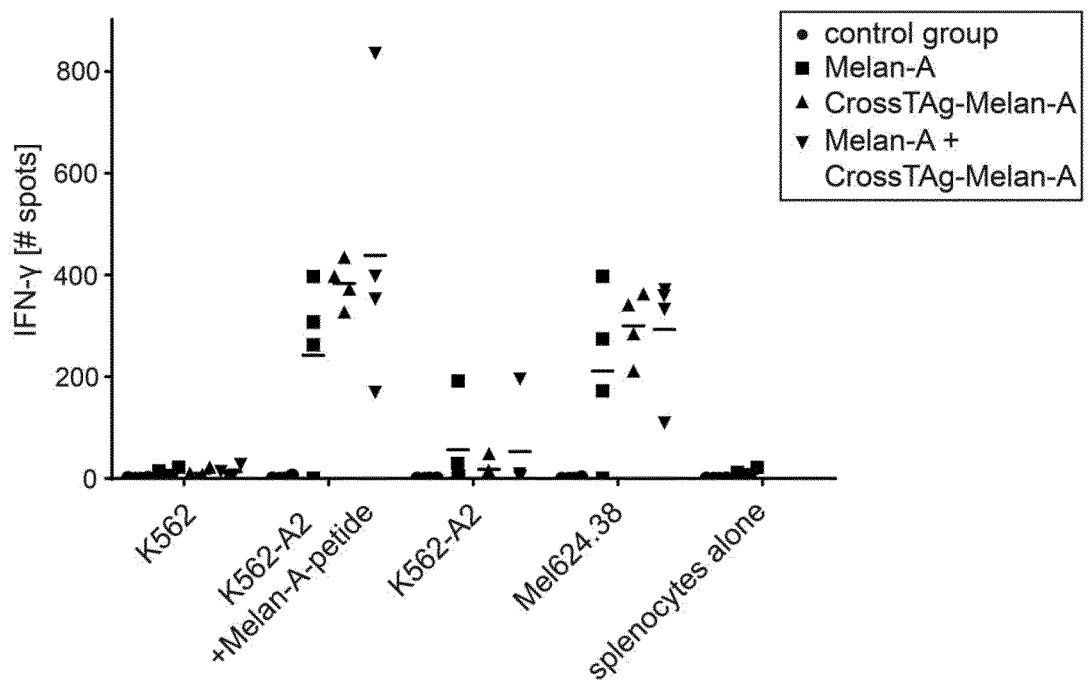
Figure 4:
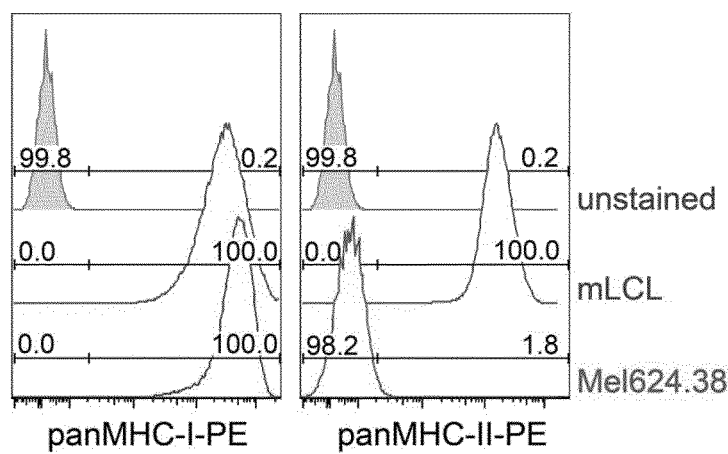

FIG. 4: Capability of cytokine secretion by Melan-A specific CD8+ T cells.

(A) Reactivity of Melan-A specific CD8+ T cells was investigated by IFN-γ secretion 10 days after in vitro restimulation of the splenocytes. Expanded splenocytes were cocultured in a 1:1 ratio with target cells for 24 hours. Applied target cells were K562 cells (MHC-I and -II negative), K562-A2 (HLA-A02:01+) incubated with or without Melan-A-peptide for 2 hours and Mel624.38 (HLA-A02:01+, Melan-A+). Number of IFN-γ spots was detected with an ELISpot-reader (C.T.L.). Every data point shown in the graph represents the number of FN-g spots from activated T cells derived from one mouse. Analyzed were three individual experiments with a total of 16 mice in each experiment (one exemplary experiment shown). (B) MHC-I and -II expression on the target cell line Mel624.38 was analyzed using monoclonal panMHC-I or panMHC-II antibodies. Mini-Epstein-Barr virus-(EBV)-transformed lymphoblastoid cell line (mLCL) served as a positive control, unstained cells functioned as a negative control.

Figure 5:
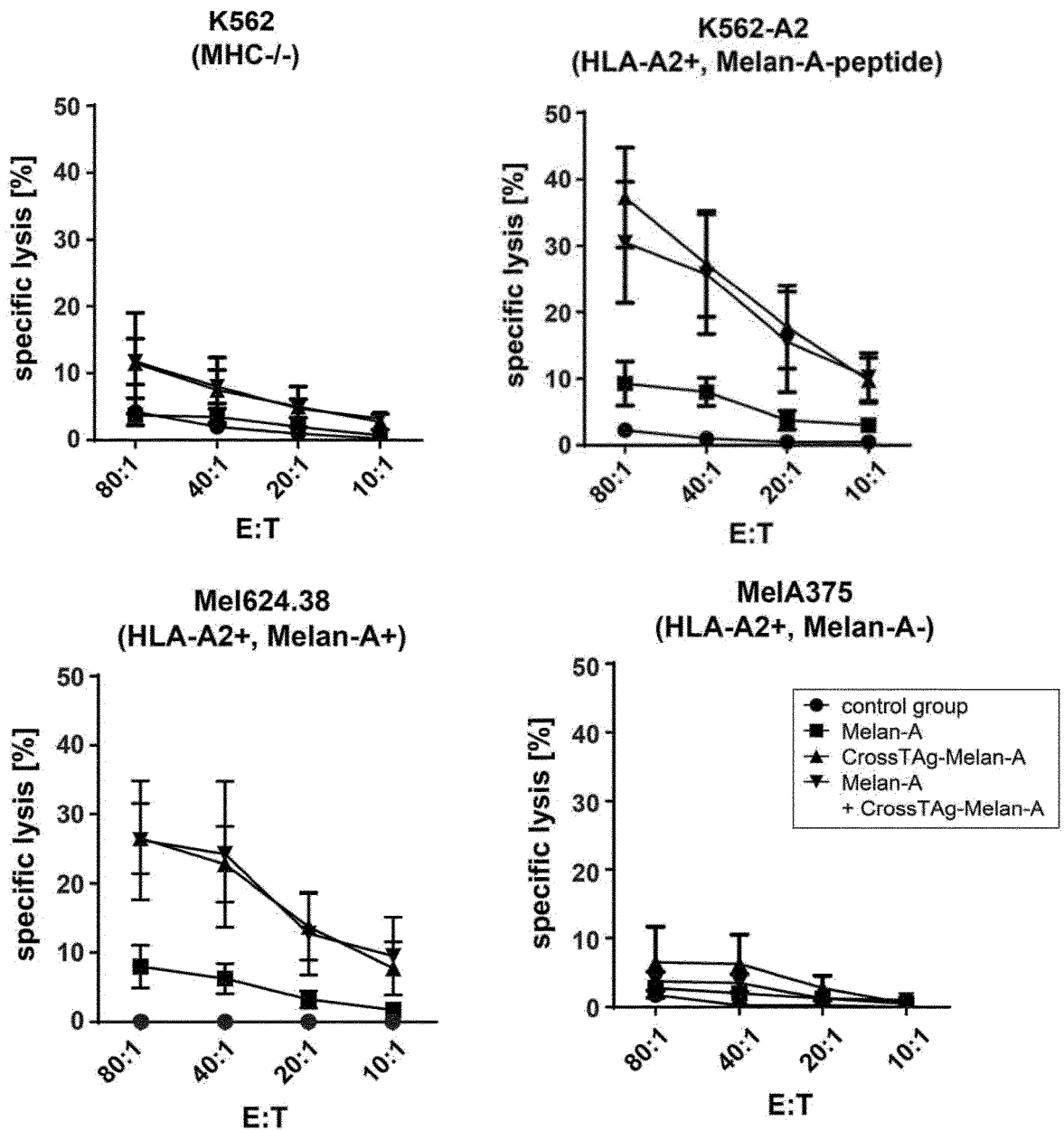

FIG. 5: Killing capacity of expanded splenocytes.

Target cells were labeled with radioactive chromium which can be detected in the supernatant if the cells were lysed. Different tumor cell lines were used as target cells. Expanded splenocytes were cocultured in different ratios with target cells (splenocytes:APC=80:1; 40:1; 20:1; 10:1) for 4 hours before released radioactive chromium in the supernatants was measured. Various target cells were applied: to envision the NK cell activity within the splenocyte population K562 (MHC-I-/-II-) were chosen. As positive controls K562-A2 (Melan-A-, HLA-A*02:01+) loaded with Melan-A-peptide or Mel624.38 (Melan A+, HLA-A*02:01+) were used. MelA375 (Melan A-, HLA-A*02:01+) served as a negative control. Every data point shown in the graph represents the mean value shown with standard deviation calculated from two measured values. Analyzed were three individual experiments with a total of 16 mice in each experiment (one exemplary experiment shown).

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

As used herein, the term "expression" refers to the process by which a polypeptide is produced based on the nucleic acid sequence of a gene. Accordingly, the term "expressed" protein or polypeptide comprises, without limitation, intracellular, transmembrane and secreted proteins or polypeptides.

Technical terms are used by their common sense. If a specific meaning is conveyed to certain terms, definitions of terms will be given in the following in the context of which the terms are used.

One aspect of the present invention refers to a dendritic cell composition comprising dendritic cells expressing an antigen or fragment thereof wherein the antigen or fragment thereof is fused to a targeting signal sequence that promotes the MHC II presentation of the antigen or fragment thereof.

More specifically, the present invention refers to a dendritic cell composition comprising dendritic cells expressing at least one fusion protein comprising
- at least one antigen or a fragment thereof,
- an endoplasmatic reticulum (ER)-translocation signal sequence preceding the N-terminus of the antigen or fragment thereof, and
- a transmembrane and cytoplasmic domain comprising an endosomal/lysosomal targeting sequence following the C-terminus of the antigen or fragment thereof.

The fragment may be a sequence of the antigen that is specific for this antigen, i.e. does not occur in another protein or peptide of a mammal, especially of a human. The fragment may be shorter than the sequence of the antigen, such as at least 5%, at least 10%, at least 30%, at least 50%, at least 70%, at least 90% shorter than the antigen. The fragment may have a length of at least 9, at least 10, at least 11, at least 12, at least 13, at least 14, at least 15 or more amino acids.

The administration of a dendritic cell composition comprising dendritic cells expressing the antigen fused to a targeting signal sequence leads to an increase of the antigen specific $CD8^+$ T cells compared to the administration of a dendritic cell composition comprising dendritic cells expressing the conventional antigen without fusion to a targeting signal sequence. Therefore dendritic cells expressing the antigen fused to a targeting signal sequence provide a superior induction capacity, an improved capability of IFN-γ secretion upon stimulation and a high killing capacity compared to dendritic cells solely expressing the conventional antigen without fusion to a targeting signal sequence.

In a specific embodiment the dendritic cell composition further comprises dendritic cells expressing at least one antigen or a fragment thereof wherein the antigen is not fused to a targeting signal sequence that promotes the MHC II presentation of the antigen or fragment thereof.

That means that the dendritic cell composition comprises (i) dendritic cells expressing at least one antigen which is fused to a targeting signal sequence that promotes the MHC II presentation of the antigen or fragment thereof and (ii) dendritic cells expressing at least one antigen or fragment thereof which is not fused to a targeting signal sequence that promotes the MHC II presentation of the antigen or fragment thereof.

In other words, the present invention refers to a dendritic cell composition comprising
- (i) dendritic cells expressing at least one fusion protein comprising
  - at least one antigen or a fragment thereof,
  - an endoplasmatic reticulum (ER)-translocation signal sequence preceding the N-terminus of the antigen or fragment thereof, and
  - a transmembrane and cytoplasmic domain comprising an endosomal/lysosomal targeting sequence following the C-terminus of the antigen or fragment thereof, and
- (ii) dendritic cells expressing at least one antigen or a fragment thereof without
  - an endoplasmatic reticulum (ER)-translocation signal sequence preceding the N-terminus of the antigen or fragment thereof, and
  - a transmembrane and cytoplasmic domain comprising an endosomal/lysosomal targeting sequence following the C-terminus of the antigen or fragment thereof.

In a preferred embodiment, the antigen of (i) and (ii) is the same antigen. For example, this means that a specific embodiment of the invention refers to a dendritic cell composition comprising
- (i) dendritic cells expressing at least one fusion protein comprising
  - MELAN-A antigen or a fragment thereof,
  - an endoplasmatic reticulum (ER)-translocation signal sequence preceding the N-terminus of the MELAN-A antigen or a fragment thereof, and
  - a transmembrane and cytoplasmic domain comprising an endosomal/lysosomal targeting sequence following the C-terminus of the MELAN-A antigen or a fragment thereof, and
- (ii) dendritic cells expressing the MELAN-A antigen or a fragment thereof without
  - an endoplasmatic reticulum (ER)-translocation signal sequence preceding the N-terminus of the MELAN-A antigen or fragment thereof, and
  - a transmembrane and cytoplasmic domain comprising an endosomal/lysosomal targeting sequence following the C-terminus of the MELAN-A antigen or fragment thereof.

The administration of a mixture of dendritic cells expressing the antigen fused to a targeting signal sequence and dendritic cells expressing the antigen without fusion to a targeting signal sequence leads to an increase of the antigen specific $CD8^+$ T cells. Therefore, said mixture provides a superior induction capacity compared to dendritic cells solely expressing the antigen without fusion to a targeting signal sequence or dendritic cells solely expressing the antigen with fusion to a targeting signal sequence. The mixture also showed a high capability of IFN-γ secretion upon stimulation and a high killing capacity.

The antigen be it with or without fusion to a targeting signal sequence that promotes MHC II presentation may be introduced into the dendritic cells, for example by means of transient expression or stable expression. In other words, expression of the antigen, be it with or without fusion to a targeting signal sequence that promotes MHC II presentation, may be transient expression or stable expression. In preferred embodiments the expression is transient expression, for example by introducing ivt-RNA coding for the at least one fusion protein. The expression of ivt-RNA has the advantage that quality-controlled ivt-RNA can be rapidly produced and carries no immunogenic protein contaminants.

The ER translocation signal sequence may be derived from an endosomal/lysosomal associated protein.

The ER-translocation signal sequence used in the disclosed method may be the sorting sequence of an endosomal/lysosomal localized protein. Endosomal/lysosomal localized proteins as used herein refer to proteins which are localized in the membrane or the lumen of the endosomes and/or the lysosomes of a cell.

Examples for endosomal or lysosomal localized proteins are glycosidases such as, alpha-galactosidase A/GLA, endo-beta-N-acetylglucosaminidase H/Endo H, alpha-N-acetyl-galactosaminidase/NAGA, galactosylceramidase/GALC, alpha-N-acetylglucosaminidase/NAGLU, glucosylceramidase/GBA, alpha-galactosidase/a-Gal, heparanase/HPSE, alpha-L-fucosidase, heparinase I, tissue alpha-L-fucosidase/FUCA1, heparinase II, beta-galactosidase-1/GLB1, heparinase III, beta-glucuronidase/GUSB, hexosaminidase A/HEXA, beta (1-3)-galactosidase, hyaluronan Lyase, beta (1-4)-galactosidase, hyaluronidase 1/HYAL1, chitinase 3-like 1, hyaluronidase 4/HYAL4, chitinase 3-like 2, alpha-L-iduronidase/IDUA, chitinase 3-like 3/ECF-L, chitobiase/CTBS, chitotriosidase/CHIT1, lactase-like protein/LCTL, chondroitin B Lyase/chondroitinase B, lysosomal alpha-glucosidase, chondroitinase ABC, MBD4, chondroitinase AC, NEU-1/Sialidase-1, cytosolic beta-glucosidase/GBA3, O-GlcNAcase/OGA, endo-beta-N-acetylglucosaminidase F1/Endo F1, PNGase F, endo-beta-N-acetylglucosaminidase F3/Endo F3, SPAM1; lysosomal proteases such as, AMSH/STAMBP, cathepsin H, cathepsin 3, cathepsin K, cathepsin 6, cathepsin L, cathepsin 7/cathepsin 1, cathepsin 0, cathepsin A/lysosomal carboxypeptidase A, cathepsin S, cathepsin B, cathepsin V, cathepsin C/DPPI, cathepsin X/Z/P, cathepsin D, galactosylceramidase/GALC, cathepsin F, oegumain/asparaginyl endopeptidase; sulfatases such as arylsulfatase A/ARSA, iduronate 2-sulfatase/IDS, arylsulfatase B/ARSB, N-acetylgalactosamine-6-sulfatase/GALNSv, arylsulfatase G/ARSG, sulfamidase/SGSH, glucosamine (N-acetyl)-6-sulfatase/GNS, sulfatase-2/SULF2; or other lysosomal proteins such as BAD-LAMP/LAMP5; hyaluronidase 1/HYAL1; CD63; LAMP1/CD107a; CD-M6PR; LAMP2/CD107b; clathrin Heavy Chain 1/CHC17; Rab27a; clathrin Heavy Chain 2/CHC22; UNC13D, CD68, CD1b or DC-LAMP.

The ER translocation signal sequence may be derived from an endosomal/lysosomal associated protein. The endosomal/lysosomal associated protein may be LAMP1, LAMP2, DC-LAMP, CD68 or CD1b, preferably LAMP1. Preferably, the ER translocation signal is human. The ER translocation signal sequence may comprise the sequence of at least one of SEQ ID NO: 1, SEQ ID NO: 6, SEQ ID NO: 8, SEQ ID NO: 10 and SEQ ID NO: 12. In some embodiments the ER translocation signal sequence may comprise the sequence of at least one of the sequences selected from the group consisting of SEQ ID NO: 2, SEQ ID NO: 7, SEQ ID NO: 9, SEQ ID NO: 11, SEQ ID NO: 13. In some embodiments the ER translocation signal sequence may consist of one of the sequences selected from the group consisting of SEQ ID NO: 2, SEQ ID NO: 7, SEQ ID NO: 9, SEQ ID NO: 11, SEQ ID NO: 13. In specific embodiments the ER translocation signal sequence comprises the sequence SEQ ID NO: 1 or a fragment thereof. In more specific embodiments the ER translocation signal sequence consists of the sequence SEQ ID NO: 2.

The endosomal/lysosomal targeting sequence may be derived from LAMP1 or DC-LAMP, preferably DC-LAMP. The endosomal/lysosomal targeting sequence is typically a part of a transmembrane and cytoplasmic domain. Thus, the transmembrane and cytoplasmic domain comprising an endosomal/lysosomal targeting sequence may be derived from LAMP1 or DC-LAMP, preferably DC-LAMP. Preferably the transmembrane and cytoplasmic domain comprising an endosomal/lysosomal targeting sequence is human. Typically the endosomal/lysosomal targeting sequence comprises the motif Y-XX followed by a hydrophobic amino acid (SEQ ID NO: 4). Preferably, the endosomal/lysosomal targeting signal sequence is YQRI (SEQ ID NO: 5). For example, the transmembrane and cytoplasmic domain comprising an endosomal/lysosomal targeting sequence may comprise the sequence SEQ ID NO: 14 or a fragment thereof.

The term hydrophobic amino acid is well known to the skilled person. Examples for hydrophobic amino acids are Ala, Ile, Leu, Phe, Val, Pro, Gly, Met, Trp, Tyr, Pro, Cys.

The dendritic cells may comprise different populations of antigen presenting cells, each population expressing a different antigen fusion protein.

Typically, the dendritic cells are mature dendritic cells, generated by a method comprising the following steps: i) provision of monocytes; ii) incubation of the monocytes of step i) with IL-4 and GM-CSF; iii) incubation of the monocytes of step ii) with IL-4 and GM-CSF in combination with a maturation cocktail.

The maturation cocktail may comprise at least one of the components selected from the group consisting of IL-ß, TNF-α, IFN-γ, TLR7/8 agonist, PGE2 and TLR3 agonist or a combination thereof. The TLR7/8 agonist may be R848 or CL075. The TLR3 agonist may be poly(I:C). For example, the maturation cocktail may comprise a combination of IFN-γ, TLR7/8 agonist, PGE2, such as a combination of IFN-γ, TLR7/8 agonist, PGE2, and TLR3 agonist. In a specific embodiment, the maturation cocktail may comprise a combination of IL-ß, TNF-α, IFN-γ, TLR7/8 agonist and PGE2. In another specific embodiment, the maturation cocktail may comprise a combination of IL-ß, TNF-α, IFN-γ, TLR7/8 agonist, PGE2 and TLR3 agonist. The invention also relates to maturation cocktails as described herein. Further, the invention also relates to in vitro maturation of at least one immature dendritic cell, comprising stimulating at least one immature dendritic cell with the maturation cocktails as described herein.

The incubation of step ii) may last for at least 2 days. The incubation of step iii) may last for at least 12 hours, preferably 24 hours.

Typically, the antigen is a tumor antigen or a viral antigen. The tumor antigen may be selected from the group consisting of viral tumor antigen, tumor-specific antigen, tumor associated antigen and an antigen carrying patient specific mutations and being expressed in tumor cells of the patient. Preferably the antigen carrying patient specific mutations and being expressed in tumor cells of the patient is not expressed in non-cancerous cells of the patient.

Viral tumor antigens also termed oncogenic viral antigens are antigens of oncogenic viruses, such as the oncogenic DNA viruses for example viruses, such as hepatitis B viruses, herpesviruses, and papillomaviruses and oncogenic RNA viruses. Tumor specific antigens refer to tumor associated mutations which are exclusively expressed by tumor cells. The group of tumor associated antigens comprises for example tissue specific cancer/testis antigens or tissue differentiation antigens such as MART-1 (MELAN-A), Tyrosinase or CD20. The tumor antigen may be a tumor associated antigen, optionally the tumor associated antigen is a cancer/testis antigen (C/T antigen). The C/T antigen may be selected from the group comprising of MAGE family members, for example MAGE-A1, MAGE-A3, MAGE-A4, but not limited to these, tumor antigens comprising single point mutations, NY-ESO1, tumor/testis-antigen 1B, GAGE-1, SSX-4, XAGE-1, BAGE, GAGE, SCP-1, SSX-2, SSX-4, CTZ9, CT10, SAGE and CAGE. Preferably the C/T antigen may be selected from the group consisting of GAGE-1, SSX-4 and XAGE-1. Preferably the tumor antigen is a tissue differentiation antigen such as MART-1, Tyrosinase or CD20.

More preferably the tumor antigen is MART-1, which is also known as MELAN-A. Thus, in specific embodiments the invention refers to a dendritic cell composition comprising dendritic cells expressing at least one fusion protein comprising
- at least one antigen or a fragment thereof,
- an endoplasmatic reticulum (ER)-translocation signal sequence preceding the N-terminus of the antigen or fragment thereof, and
- a transmembrane and cytoplasmic domain comprising an endosomal/lysosomal targeting sequence following the C-terminus of the antigen or fragment thereof;
- wherein the fusion protein is MELAN-A.

Specific embodiments of the invention refer to a dendritic cell composition comprising dendritic cells expressing at least one antigen or a fragment thereof wherein the antigen is not fused to a targeting signal sequences that promotes the MHC II presentation of the antigen or fragment thereof wherein said dendritic cells do not express an antigen or fragment thereof wherein the antigen is fused to a targeting signal sequence that promotes the MHC II presentation of the antigen or fragment thereof, wherein the antigen is MELAN-A.

In specific embodiments, the dendritic cell composition comprises (i) dendritic cells expressing at least one antigen which is fused to a targeting signal sequence that promotes the MHC II presentation of the antigen or fragment thereof and (ii) dendritic cells expressing at least one antigen or fragment thereof which is not fused to a targeting signal sequence that promotes the MHC II presentation of the antigen or fragment thereof and dendritic cells, wherein the antigen is MELAN-A.

Therefore, the invention refers also the dendritic cell composition for use as a medicament. Also contemplated is a dendritic cell vaccine for use as a medicament.

Another aspect of the invention refers to the dendritic cell composition for use in the treatment of cancer. Specific embodiments relate to the dendritic cell composition for use in stimulating an immune response against a melanoma-associated antigen.

A further aspect of the invention refers to the dendritic cell vaccine for use in the treatment of cancer. Specific embodiments relate to the dendritic cell vaccine for use in stimulating an immune response against a melanoma-associated antigen.

The activation profile of the treatment with the composition of the invention can be determined for example by measuring activation-induced cytokine release or antigen-directed killing capacity of T cells isolated from an organism to which the dendritic cell composition of the invention is administered.

To measure activation-induced cytokine secretion, T cells may be co-cultured with antigen-loaded dendritic cells. Different effector cell to target cell (E:T) ratios may be employed. T cells incubated with control antigen presenting, i.e. mock-transfected APCs, or in the absence of stimulating cells may be used as negative controls. The culture supernatants are assessed by a standard enzyme-linked immunosorbent assay (ELISA). Examples for markers are, without limitation, granulocyte-macrophage colony-stimulating factor (GM-CSF), interferon-γ (IFN-γ), IL-2 and TNF-α secretion. IFN-γ, IL-2 and TNF-α secretion upon antigen encounter correlates with enhanced anti-tumor function and is therefore particularly useful when measuring antigen-induced cytokine secretion of CD8$^+$ cytotoxic T cells. Additionally, IFN-γ and granulocyte-macrophage colony-stimulating factor (GM-CSF) are well-defined cytokines for the assessment of antigen-specific CD4$^+$ T helper-1 (Th1)-polarized T cell clones.

The cytotoxic activity of T cells activated by the dendritic cell population of the invention may be measured for example by chromium release assays. In such assays, target cells are labeled with radioactive chromium and exposed to T cells. Upon killing, radioactive chromium is released into the supernatant and detectable within 4 hours after the start of the co-culture. Specific chromium release is normalized to spontaneous release assessed by incubating target cells in the absence of effector cells. Accordingly, high amounts of chromium in the supernatant correlate with excellent cytolytic T cell activity. Chromium release assays are preferably performed to screen for tumor antigen-specific CD8$^+$ T cells.

Donor derived antigen presenting cells may be for example isolated monocytes which are maturated to dendritic cells. Maturated dendritic cells exhibit optimal activation capacity.

Typically, the dendritic cells are autologous cells, i.e. cells obtained from a patient which are treated according to teaching of the invention and then administered to the same patient. For example, monocytes are isolated from a patient, matured to dendritic cells and treated as described herein to express the desired antigen and then administered to the same patient.

The present invention refers also to a dendritic cell vaccine comprising the dendritic cell composition as described herein.

The active components of the present invention, such as the dendritic cell composition, are preferably used in a pharmaceutical composition, in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component, i.e. the dendritic cells of the invention. The choice of the carrier is dependent on the application.

The pharmaceutical composition may contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, Pa., latest edition. An appropriate application is a parenteral application, for example intradermal, intramuscular, subcutaneous, intramedular injections as well as intrathecal, direct intraventricular, intravenous, intranodal, intraperitoneal or intratumoral injections. The intravenous injection is the preferred treatment of a patient.

The pharmaceutical composition may be an injectable composition i.e. a pharmaceutically acceptable fluid composition comprising at least one active ingredient, e.g. a dendritic cell composition of the invention. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the dendritic cells of this disclosure are conventional; appropriate formulations are well known to those of ordinary skill in the art.

Formulations suitable for parenteral administration, such as, by intraarticular (in the joints), intravenous, intramuscular, intradermal, intracutan, intraperitoneal, and subcutaneous routes (preferably intradermal, intranodal, intracutan or subcutaneous) include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intradermal, intracutan, subcutan or intranodal administration are the preferred method of administration for dendritic cells of the invention.

The dose of the dendritic cells administered to a patient, in the context of the present invention should be sufficient to effect a beneficial therapeutic response in the patient over time, or to inhibit growth of cancer cells, or to inhibit infection. Thus, cells are administered to a patient in an amount sufficient to elicit an effective CTL response to the virus or tumor antigen and/or to alleviate, reduce, cure or at least partially arrest symptoms and/or complications from the disease or infection. An amount adequate to accomplish this is defined as a "therapeutically effective dose." The dose will be determined by the activity of dendritic cell produced and the condition of the patient. The size of the dose also will be determined by the existence, nature, and extent of any adverse side-effects that accompany the administration of a particular cell in a particular patient. In determining the effective amount of the cell to be administered in the treatment or prophylaxis of diseases such as cancer, the physician needs to evaluate CTL toxicity, progression of the disease, and the induction of immune response against any introduced cell type.

Prior to administration, blood samples are obtained and saved for analysis. Generally, at about $10^4$ to $10^6$ and more preferably $10^6$ to $10^{10}$ cells are administered into a 70 kg patient in form of a single dose or multiple doses via intracutan, intranodal, subcutan or intradermal injection. Preferably, cell numbers of at least $2*10^6$-$10^7$ pervaccination are used. The injections may be administered once per week for a period of 4 weeks followed by 1 administration/injection per month and should be given preferably near lymph nodes, directly into lymph nodes or by intradermal, intracutan or subcutaneous injections. Booster injections may additionally be performed. As stated, cell reinfusions are preferably repeated every month for a total of 10-12 treatments in a one-year period. After the first treatment, infusions can be performed on an outpatient basis at the discretion of the clinician. If the reinfusion is given as an outpatient, the participant is monitored for at least 4 hours following the therapy.

The dendritic cell composition/dendritic cell vaccine may be administered at least once, at least twice, at least 3, at least 4, at least 5, at least 6, at least 7, at least 8, at least 9, at least 10 times. The vaccine may be administered not more than 15 times, 18 times, 20 times, 25 times, 30 times. The interval between the administrations is at least 3 days, at least 7 days, at least 14 days or at least 4 weeks. Preferably the vaccine is administered once a week for a period of 4 weeks followed by 1 administration per month for a total of 10 to 12 treatments.

For administration, cells of the present invention can be administered at a rate determined by the LD-50 (or other measure of toxicity) of the cell type, and the side-effects of the cell type at various concentrations, as applied to the mass and overall health of the patient. Administration can be accomplished via single or divided doses. The cells of this invention can supplement other treatments for a condition by known conventional therapy, including cytotoxic agents, nucleotide analogues and biologic response modifiers. Similarly, biological response modifiers are optionally added for treatment by the dendritic cells.

The invention also relates to a composition, comprising
a) an expression vector comprising
   a human ER-translocation signal sequence,
   a human transmembrane and cytoplasmic domain comprising an endosomal/lysosomal targeting sequence, and
   at least one antigen or fragment thereof; and
b) an expression vector comprising at least one antigen or fragment thereof, but lacking an ER-translocation signal sequence and a human transmembrane and cytoplasmic domain comprising an endosomal/lysosomal targeting sequence.

The invention further relates to a kit, comprising:
a) an expression vector comprising
   a human ER-translocation signal sequence,
   a human transmembrane and cytoplasmic domain comprising an endosomal/lysosomal targeting sequence, and
   at least one antigen or fragment thereof; and
b) an expression vector comprising at least one antigen or fragment thereof, but lacking an ER-translocation signal sequence and a human transmembrane and cytoplasmic domain comprising an endosomal/lysosomal targeting sequence.

A "vector" is any molecule or composition that has the ability to carry a nucleic acid sequence into a suitable host cell where synthesis of the encoded polypeptide can take place. Typically and preferably, a vector is a nucleic acid that has been engineered, using recombinant DNA techniques that are known in the art, to incorporate a desired nucleic acid sequence (e.g., a nucleic acid of the invention). The vector may comprise DNA or RNA and/or comprise liposomes. The vector may be a plasmid, shuttle vector, phagemide, cosmid, expression vector, retroviral vector, adenoviral vector or particle and/or vector to be used in gene therapy. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

Examples 1.1 Activation of Melan-A Specific CD8+ T Cells in a NSG Mouse Model

To develop a humanized mouse model to study our DC vaccination in vivo, we used NOD-scid/Il2rγ-/- (NSG) mice xenografted with human PBMC. As NSG mice are immune deficient (lacking NK, T and B cells) (SPRANGER, S. et al. 2012. NOD/scid IL-2Rg(null) mice: a preclinical model system to evaluate human dendritic cell-based vaccine strategies in vivo. *J Transl Med*, 10, 30.), the resulting niche in the immune cell population allows a very efficient engraftment with human PBMC (SHULTZ, et al. 2007. Humanized mice in translational biomedical research. *Nat Rev Immunol*, 7, 118-30.).

16 NSG recipient mice were divided into four groups and xenografted with human HLA-A*02:01 PBMC over 14 days. Vaccination of mice in different groups consisted of two intravenous injections of autologous freshly prepared mature dendritic cells electroporated with either CrossTAg-Melan-A-ivt-RNA, conventional Melan-A-ivt-RNA or mixed ivt-RNA given twice with a one-week interval between injections. After a further seven days, and after a subsequent in vitro restimulation, splenic populations were analyzed by FACS to enumerate Melan-A-specific CD8+ T cells. Cytotoxicity and the capability of secreting IFN-γ of Melan-A-specific T cells of all 4 groups were also analyzed by chromium-release and ELISpot assays (FIG. 1).

1.2 Maturation Status and Melan-A-Expression of Transfected Mature Dendritic Cells Monocytes derived from a healthy HLA-A*02:01-donor were isolated and matured as described in Spranger et al. (2010. Generation of Th1-polarizing dendritic cells using the TLR7/8 agonist CL075. J Immunol, 185, 738-47) in vitro within 3 days. To verify the in vitro maturation of dendritic cells for later administration to humanized mice in vivo, we determined expression of cell surface molecules typically expressed on immature dendritic cells and mature dendritic cells by FACS analysis (Burdek et al. 2010. Three-day dendritic cells for vaccine development: antigen uptake, processing and presentation. J Transl Med, 8, 90). Analyzed dendritic cells expressed a mature phenotype (FIG. 2 A). Mature dendritic cells were transfected with either CrossTAg-Melan-A- or conventional Melan-A-ivt-RNA following electroporation conditions for mature 3d dendritic cells (Burdek et al., 2010). Transfection efficiency was examined (6 hours after electroporation) by intracellular staining of Melan-A protein with monoclonal antibodies (FIG. 2 B).

1.3 Quantification of Melan-A Specific CD8+ T Cells

Reconstituted mice were vaccinated twice, with a one-week interval, before splenic cells were isolated and analyzed. To compare the induction efficiency of the different DC vaccines, the number of Melan-A specific CD8+ T cells was detected by a fluorescence-labeled HLA-A*02:01-multimer loaded with a Melan-A-epitope (FIG. 3 A). The ex vivo analysis of splenic cells already revealed a higher number of Melan-A-specific CD8+ T cells in the CrossTAg-DC-group or mixed group compared to the conventional DC group, which showed only a slightly higher number of specific cells compared with the control group. Moreover, we detected a significantly higher percentage of CD8+ T cells in the CrossTAg-group compared to the conventional-group (FIG. 3 B). Subsequently, remaining splenocytes were further expanded in vitro by Melan-A transfected dendritic cells and hIL-2, whereas the control group was only treated with hIL-2. Reanalysis of expanded cells demonstrated an even clearer discrepancy between CrossTAg-Melan-A-containing dendritic cells and conventional Melan-A dendritic cells concerning the average number of Melan-A specific CD8+ T cells. A significantly greater number of Melan-A-specific CD8+ T cells could be seen in the CrossTAg-group compared with the conventional-group (FIG. 3 C). Thus, vaccination with dendritic cells loaded with CrossTAg-Melan-A-ivt-RNA resulted in a superior induction-capacity, demonstrated by greater proliferation of Melan-A specific CD8+ T cells. An even stronger induction-capacity is demonstrated for the vaccination with a combination of dendritic cells loaded with CrossTAg-Melan-A-ivt-RNA and dendritic cells loaded with Melan-A-ivt RNA without fusion to the CrossTAg.

1.4 Functional Analysis of Induced Melan-A Specific CD8+ T Cells

We demonstrated a superior induction efficiency of antigen-specific CD8+ T cells by CrossTAg-transfected dendritic cells indicating a clear benefit of RNA constructs having included CrossTAg-sequences flanking the target antigen. For the establishment of a CD8+ T cell memory as well as for successful tumor regression a pivotal role of CD4+ T cells has been previously shown (Mortenson, et al. 2013. Effective anti-neu-initiated antitumor responses require the complex role of CD4+ T cells. *Clin Cancer Res*, 19, 1476-86; Rosenberg et al. Cancer immunotherapy: moving beyond current vaccines. Nat Med, 10, 909-15). Thus, the enhanced immune response induced in NSG mice vaccinated with CrossTAg-Melan-A-containing dendritic cells might be explained by the enabled CD4+ T cell help provided by the CrossTAg-sequences leading to the Melan-A-presentation on MHC-I and -II.

To further examine the functionality of the induced T cells, the next important issue to clarify was whether the induced Melan-A specific CD8+ T cells were also able to secret IFN-γ which is critical for an appropriate immune response. Thus, the capability of Melan-A specific CD8+ T cells to secrete IFN-γ upon stimulation was analyzed. In vitro expanded splenocytes were cocultured with various tumor cell lines as stimulating cells to evaluate IFN γ secretion. Unstimulated splenocytes were found to be completely unreactive. NK cell activity, within in the splenocyte population, was determined by using the HLA-negative tumor cell line K562, as NK cells are activated by target cells lacking any MHC molecules. No NK cell activity was detected. Only stimulator cells expressing Melan-A or loaded with specific peptide led to a strong activation of splenocytes, whereas Melan-A-negative cells did not stimulate the splenocytes. In average, more IFN-γ spots could be detected from CD8+ T cells isolated from CrossTAg- or the mixed group compared to the conventional group or the control group (FIG. 4 A).

To address the question whether the reactivity observed in the ELISpot assay could be traced back to CD8+ T cells and not to CD4+ T cells as well, the MHC-II expression on the stimulator cells was examined. The stimulator cell line was positive for MHC-I but not for MHC-II (FIG. 4 B). Even after IFN-γ treatment of stimulator cells overnight did not lead to an induced expression of MHC-II molecules (data not shown). Thus, only MHC-I-restricted T cells could be activated, indicating that the observed reactivity was originating from activated CD8+ T cells, as CD4+ T cells would require antigen-presentation on MHC-II to be activated.

It is also important for CD8+ T cells to be cytotoxic in order to be able to kill tumor cells. Therefore, cytotoxic capacity of Melan A-specific T cells was assessed by a chromium-release assay (FIG. 5). The cytotoxicity results demonstrated that expanded splenocytes specifically lysed only Melan-A-peptide presenting cells but not the control cell line which was negative for the target antigen. Cells from the control group did not show any killing activity. The NK cell activity was also very low within splenocytes in all groups. Notably, cells from CrossTAg-DC-group and mixed group showed a much higher killing capacity compared to splenocytes from the conventional DC-group.

Methods
Genetic Constructs

The pGEM-eGFP-A120 vector was used as the starting construct for the CrossTAg-vector. This polyA120 variant of the original pGEM vector renders transcribed RNA with higher stability and led to improved protein expression. The plasmid further contained a unique AgeI site at the 5' end of the eGFP cDNA, as well as a unique EcoRI site at the 3' end. The poly-A tail is followed by a SpeI site that allows linearization of the plasmid for ivt-RNA production.

The pGEM-CrossTAg-A120 plasmid was cloned by replacing eGFP with cDNA coding for the CrossTAg targeting signal. The CrossTAg sequence consists of the ER-translocation signal of the human lysosome-associated membrane protein-1 (LAMP-1, accession: NP_005552, aa 1-28) fused 5' to the transmembrane and cytoplasmic domain of DC-LAMP (accession: NP_055213, aa 376-416). For insertion of antigen-encoding cDNA, the distinct Cross-TAg sequences are separated by an 18-bp spacer containing NheI, KpnI and PstI restriction sites without disrupting the LAMP1 open reading frame (ORF). The codon optimized Cross-TAg sequence was designed virtually using computational cloning software and synthesized by (GeneArt, Regensburg, Germany). The complete CrossTAg sequence was subsequently cut from plasmid DNA using AgeI (5' end) and EcoRI (3' end) restriction sites and ligated into the MCS of the equally digested pGEM-A120 vector. For cloning of various C/T antigen-CrossTAg constructs (pGEM-GAGE-1-CrossTAg-A120, pGEM-MAGE-A4-CrossTAg-A120, pGEM-NY-ESO-1-CrossTAg-A120, pGEM-SSX-4-Cross-TAg-A120, pGEM-XAGE-1-CrossTAg-A120) antigen cDNA was amplified from plasmids by PCR (accessions: GAGE-1, U19142; MAGE-A4, NM 001011550; NY-ESO1, AJ003149; SSX-4, U90841; XAGE-1, AF251237) using forward and reverse gene-specific primers and ligated via NheI and PstI/NotI restriction sites. All antigen sequences were inserted into the split CrossTAg signal of pGEM-CrossTAg-A120 without disrupting the initial ORF.

For the validation of CD4$^+$ T cell epitopes, complementary oligonucleotides were synthesized (Metabion, Planegg, Germany) and annealed. Cohesive ends, generated upon annealing, were used for direct ligation of these short antigen sequences into the CrossTAg vector.

Production of ivt-RNA

Following SpeI linearization, pGEM-plasmids were used as templates for single-species in vitro transcribed (ivt)-RNA production using the mMESSAGE mMACHINE T7 kit (ThermoFisher Scientific, Massachusetts, USA), according to the manufacturer's instructions. For quality control, ivt-RNA product length was analyzed by agarose gel electrophoresis. Concentration and purity were determined by means of the Nanodrop ND-1000 spectrophotometer (ThermoFisher Scientific, Massachusetts).

Cell Culture

Monocyte-derived 3d mature dendritic cells were generated and transfected as described in Biirdek et al. (Journal of Translational Medicine 2010, 8:90.) RNA transfection of mature dendritic cells: Mini-Epstein-Barr virus-(EBV)-transformed lymphoblastoid cell lines (mLCL) were achieved by electroporation.

Surface Phenotyping of Dendritic Cells

Surface markers expressed by dendritic cells were detected with the following antibodies: PE-conjugated CCR7-specific antibody (3D12) (eBioscience, Frankfurt, Germany), Hz450-conjugated CD4-specific anti-body (RPA-T4), Hz500-conjugated CD8-specific antibody (RPA-T8), FITC-conjugated CD14-specific antibody (M5E2), PE-conjugated CD40-specific antibody (5C3), PE-conjugated CD40L-specific antibody (TRAP1), PE-conjugated CD80-specific antibody (L307.4), FITC-conjugated CD83-specific antibody (HB15e), FITC-conjugated CD86-specific antibody (2331), APC-conjugated CD137-specific antibody (4B4-1), FITC-conjugated DC-SIGN-specific antibody (DCN46), PE-conjugated HLA-DR-specific antibody (G46-6) (all from BD Biosciences, Heidelberg, Germany). After washing, cells were stained for 30 min at 4° C. and propidium iodid (2 µg/ml) was added for the exclusion of dead cells. Expression of all surface markers was analyzed by flow cytometry (LSRII, BD). Post-acquisition data analysis was done using FlowJo 8 software (TreeStar). The analysis of CD40L surface expression on T cells was performed as described (Frentsch, M. et al. (2005) Direct access to CD4+ T cells specific for defined antigens according to CD154 expression. Nat Med 11(10): 1118-1124) using 2 µg/ml αCD40 antibody (clone G28.5, provided by M. Frentsch, Berlin-Brandenburg Center for Regenerative Therapies) and assessed 6 h after the start of the T cell:APC co-culture.

De Novo Priming of PBL with RNA-Transfected Dendritic Cells 3d mature dendritic cells of a healthy donor were transfected with CrossTAg-RNA coding for the MELAN-A. After electroporation the transfected mature dendritic cells were harvested and mixed mature dendritic cells of this mixture were co-cultured within a 1:2 ratio peripheral blood lymphocytes (PBL), which were non-adherent during the plastic adherence of PBMC in the process of mature dendritic cells generation. The cells were cultured at 37° C. in a humidified atmosphere. Interleukine-2 (IL-2, 20 U/ml; Chiron Behring, Marburg, Germany) and 5 ng IL-7/ml (Promokine, Heidelberg, Germany) were added after 1 day and then on every other day.

Cytokine Release Assay

To measure activation induced cytokine secretion, $5*10^4$ T cells were co-cultured with $1*10^5$ ivt-RNA-loaded antigen presenting cells DC in 200 µl T cell medium in round-bottom 96-well plates at 37° C. in a humidified atmosphere. T cells with mock-transfected APCs or without stimulator cells were used as negative controls. After 16 h of co-culture, supernatants were harvested and assessed by enzyme-linked immunosorbent assay (ELISA) using the OptEIA Human IFN-γ or GM-CSF Set (both from BD Biosciences, Heidelberg, Germany).

The invention claimed is:

1. A dendritic cell composition comprising
A) dendritic cells that express at least one fusion protein, wherein said fusion protein comprises:
   i) at least one antigen or a fragment thereof; and
   ii) at least one targeting signal sequence, wherein said targeting signal sequence comprises:
      a) an endoplasmatic reticulum (ER)-translocation signal sequence preceding the N-terminus of the antigen or fragment thereof; and
      b) a transmembrane and cytoplasmic domain comprising an endosomal/lysosomal targeting sequence following the C-terminus of the antigen or fragment thereof;
   wherein the targeting signal sequence of a) or b) promotes MHC II presentation of the antigen or fragment thereof; and
B) dendritic cells that express at least one antigen or a fragment thereof, wherein the antigen or fragment thereof is not fused to a targeting signal sequence that promotes MHC II presentation of the antigen or fragment thereof; and
   wherein the antigen of A and the antigen of B are the same antigen.

2. The dendritic cell composition according to claim 1, wherein the fusion protein and the antigen are transiently or stably expressed.

3. The dendritic cell composition according to claim 1, wherein the fusion protein and the antigen are stably expressed.

4. The dendritic cell composition according to claim 1, wherein the fusion protein and the antigen are transiently expressed by introducing ivt-RNA.

5. The dendritic cell composition according to claim 1, wherein the endosomal/lysosomal targeting sequence is derived from DC-LAMP.

6. The dendritic cell composition according to claim 1, wherein the endosomal/lysosomal targeting sequence is human.

7. The dendritic cell composition according to claim 1, wherein the endosomal/lysosomal targeting sequence comprises the sequence of SEQ ID NO: 3 or the sequence of SEQ ID NO: 14 or fragments thereof.

8. The dendritic cell composition according to claim 1, wherein the ER translocation signal sequence is derived from an endosomal/lysosomal associated protein.

9. The dendritic cell composition according to claim 8, wherein the endosomal/lysosomal associated protein is selected from the group consisting of LAMP1, LAMP2, DC-LAMP, CD68, and CD1b.

10. The dendritic cell composition according to claim 1, wherein the ER translocation signal sequence is derived from LAMP1.

11. The dendritic cell composition according to claim 1, wherein the ER translocation signal sequence comprises the sequence of SEQ ID NO: 1 or a fragment thereof.

12. The dendritic cell composition according to claim 1, wherein the dendritic cells are mature dendritic cells generated by a method comprising the following steps:
   (i) providing monocytes;
   (ii) incubating the monocytes of step i) with IL-4 and GM-CSF; and
   (iii) incubating the monocytes of step ii) with IL-4 and GM-CSF in combination with a maturation cocktail.

13. The dendritic cell composition according to claim 12, wherein the maturation cocktail comprises at least one of the components selected from the group consisting of IL-ß, TNF-α, IFN-γ, TLR7/8 agonist, PGE2, and TLR3 agonist.

14. The dendritic cell composition according to claim 13, wherein the maturation cocktail comprises a combination of IL-ß, TNF-α, IFN-γ, TLR7/8 agonist, PGE2, and TLR3 agonist.

15. The dendritic cell composition according to claim 1, wherein the antigen is MELAN-A.

* * * * *